United States Patent
Suga et al.

(10) Patent No.: US 9,410,148 B2
(45) Date of Patent: Aug. 9, 2016

(54) METHOD FOR CONSTRUCTING LIBRARIES OF NON-STANDARD PEPTIDE COMPOUNDS COMPRISING N-METHYL AMINO ACIDS AND OTHER SPECIAL (NON-STANDARD) AMINO ACIDS AND METHOD FOR SEARCHING AND IDENTIFYING ACTIVE SPECIES

(75) Inventors: Hiroaki Suga, Tokyo (JP); Yusuke Yamagishi, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 13/821,940

(22) PCT Filed: Sep. 8, 2011

(86) PCT No.: PCT/JP2011/070439
§ 371 (c)(1),
(2), (4) Date: Mar. 8, 2013

(87) PCT Pub. No.: WO2012/033154
PCT Pub. Date: Mar. 15, 2012

(65) Prior Publication Data
US 2013/0178394 A1    Jul. 11, 2013

(30) Foreign Application Priority Data
Sep. 9, 2010    (JP) .................. 2010-202012

(51) Int. Cl.
*C12N 15/10* (2006.01)
*C40B 40/10* (2006.01)
(Continued)

(52) U.S. Cl.
CPC ............... *C12N 15/1062* (2013.01); *C07K 2/00* (2013.01); *C12P 21/02* (2013.01); *C40B 30/04* (2013.01); *C40B 40/10* (2013.01); *C40B 50/06* (2013.01); *C12N 15/67* (2013.01); *C40B 20/04* (2013.01); *G01N 2500/00* (2013.01); *G01N 2500/20* (2013.01)

(58) Field of Classification Search
CPC .... C12N 15/1062; C12N 15/67; C40B 40/10; C40B 30/04; C40B 50/06; C40B 20/04; C07K 2/00; G01N 2500/00; G01N 2500/20; C12P 21/02
See application file for complete search history.

(56) References Cited

U.S. PATENT DOCUMENTS

2010/0168380 A1  7/2010  Suga et al.
2011/0275119 A1  11/2011 Suga et al.

FOREIGN PATENT DOCUMENTS

EP    1 964 916 A1   9/2008
EP    2088202 A1     8/2009
(Continued)

OTHER PUBLICATIONS

Kawakami et al. (Chemistry & Biology, 2008, 15:32-42).*
(Continued)

*Primary Examiner* — Jeremy C Flinders
(74) *Attorney, Agent, or Firm* — Birch, Stewart, Kolasch & Birch, LLP

(57) ABSTRACT

A method for screening a non-standard peptide compound in the peptide library that binds to the target substance, comprising the steps: (i) preparing a non-standard peptide library wherein a special (non-standard) amino acid is randomly incorporated into the peptide sequence by a cell-free (in vitro) translation system comprising a tRNA acylated by a special (non-standard) amino acid; (ii) bringing the obtained peptide library in contact with a target substance; and (iii) selecting a non-standard peptide that binds to the target substance as an active peptide.

12 Claims, 7 Drawing Sheets

(51) Int. Cl.
  *C40B 30/04* (2006.01)
  *C40B 50/06* (2006.01)
  *C07K 2/00* (2006.01)
  *C12P 21/02* (2006.01)
  *C40B 20/04* (2006.01)
  *C12N 15/67* (2006.01)

(56) References Cited

FOREIGN PATENT DOCUMENTS

| EP | 2141175 A1 | 1/2010 |
| EP | 2 647 720 A1 | 10/2013 |
| WO | WO 03/070740 A1 | 8/2003 |
| WO | WO 03/089454 A2 | 10/2003 |
| WO | WO 2008/059823 A1 | 5/2008 |
| WO | WO 2008/117833 A1 | 10/2008 |

OTHER PUBLICATIONS

Roberts et al. (Proc. Natl. Acad. Sci., 1997, 94:12297-12302).*
Subtelny et al. (J. Amer. Chem. Soc., 2008, 130:6131-6136).*

Higuchi, "Programmed Synthesis of Natural Product-like Non-standard Peptides Using the Translation System and Its Application", Journal of Synthetic Organic Chemistry, Japan, Mar. 1, 2010, vol. 68, No. 3, pp. 217-227, Abstract only.
PCT/ISA/210—International Search Report mailed on Nov. 8, 2011, issued in PCT/JP2011/070439.
English translation of Hayashi, "Ribosomal synthesis of nonstandard cyclic peptides and its application to drug discovery", Journal of Japanese Biochemical Society, Jun. 25, 2010, vol. 82, No. 6, pp. 505-514.
Extended European Search Report, dated Jan. 20, 2015, for European Application No. 11823628.0.
Kawakami et al., "Diverse backbone-cyclized peptides via codon reprogramming" Nature Chemical Biology, vol. 5, No. 12, Dec. 2009 (Published online Oct. 25, 2009), pp. 888-890.
Liu et al., "Evolution of Proteins with Genetically Encoded Chemical Warheads", J. Am. Chem. Soc. 2009, vol. 131 (Published online Jun. 25, 2009, pp. 9616-9617, XP-002606828.
Morimoto et al., "Discovery of Macrocyclic Peptides Armed with a Mechanism-Based Warhead: Isoform-Selective Inhibition of Human Deacetylase", Angew. Chem. Int. Ed. vol. 51, 2012, pp. 3423-3427.

* cited by examiner

| Solid-phase synthsized N-methyl peptide and derivatives | $K_D$ / nM |
|---|---|
| MCP11: CH$_2$CO-wCDV$^{Me}$SGR$^{Me}$F$^{Me}$GY$^{Me}$FPCG-NH$_2$ | 0.5 |
| MLP11: CH$_3$CO-wCDV$^{Me}$SGR$^{Me}$F$^{Me}$GY$^{Me}$FPCG-NH$_2$ | 100-1000 |
| CP11: CH$_2$CO-wCDVSGRFGYFPCG-NH$_2$ | >1000 |
| LP11: CH$_3$CO-wCDVSGRFGYFPCG-NH$_2$ | >1000 |

METHOD FOR CONSTRUCTING LIBRARIES OF NON-STANDARD PEPTIDE COMPOUNDS COMPRISING N-METHYL AMINO ACIDS AND OTHER SPECIAL (NON-STANDARD) AMINO ACIDS AND METHOD FOR SEARCHING AND IDENTIFYING ACTIVE SPECIES

TECHNICAL FIELD

The present invention relates to the generation and use of non-standard peptide libraries, for drug development, that contains a cyclic structure and/or contain a single or multiple special (non-standard) amino acid. Specifically, the invention relates to a method for constructing a library of non-standard peptide compounds containing N-methyl amino acids or other special (non-standard) amino acids, a compound library, a means to search for drug candidates from the library and the compounds found by such search.

BACKGROUND ART

1. Significance of Non-Standard Peptides

Many drugs currently on the market are low-molecular-weight organic compounds having a molecular weight of 500 Da or lower. Low-molecular-weight compounds are used because they are quickly absorbed and dispersed in the body, they often exhibit good cell membrane permeability, and are often not immunogenic. However, possible side effects amongst these molecules often result from their low selectivity. In contrast, the recently popular antibody drugs exhibit high selectivity, but they can be immunogenic, and their targets are basically limited to extracellular ones or those on cell surfaces, so their application as pharmaceutical agents is relatively limited.

Meanwhile, non-standard peptides are considered to be a group of molecules that combine the advantages of both low-molecular-weight compounds and antibodies. Developing peptide drugs has proven challenging, since peptides often exhibit low membrane permeability due to their molecular weight (1,000 to 3,000 Da) being higher than that of a low-molecular-weight organic compound, and because peptides are often rapidly degraded in vivo by proteases, thus exhibiting poor pharmacokinetic properties. However, cyclosporine, which is a naturally derived peptide, permeates cell membranes and exhibits immunosuppressive effects by binding to its target. These biological activities and pharmacokinetics result from enhanced target-binding strength, membrane permeability, and in vivo stability caused by the macrocyclic structure and the special (non-standard) amino acids in the peptide. Hence, a non-standard peptide is potentially capable of targeting not just extracellular targets but also intracellular targets. Meanwhile, significant effort has been put into developing therapeutics to inhibit defective interactions, since many diseases/disorders originate from defects in the interaction between proteins. It is normally difficult to develop inhibitors to these protein-protein interactions based on low-molecular-weight compounds, since the proteins often bind to each other via a wide area (750 to 1,500 Å) with no clear hydrophobic pockets. In contrast, non-standard peptides per se are relatively larger and have functional groups that cause static and hydrophobic interactions and enable hydrogen bonds to form. Hence, non-standard peptides could potentially bind to shallow and wide/flat binding sites on proteins in an effective manner. Thus, non-standard peptides, which are capable of binding to a wide range of extracellular/intracellular protein targets, represent an extremely attractive group of potentially new drugseeds.

2. Effects of Macrocyclic Structure and N-Methyl Amino Acid on Peptide

The macrocyclic structure provides peptides with advantages as pharmaceutical agents. 1) The macrocyclic structure limits the conformational space of the molecule and thus reduces the entropy loss when binding with the target; it thus provides the molecule with a stronger binding capacity than a straight chain structure. It has also been reported that target selectivity improves through cyclization. 2) In vivo proteases break/degrade natural polypeptides, so it binds to and cleaves straight/linear chain peptides. However, this ability of proteases to degrade cyclic peptides is much lower, and therefore in vivo stability of cyclic peptides is considerably improved. 3) It is also understood that the rigid structure improves membrane permeability. This is due to the peptide cyclization increasing the number of amide bonds forming hydrogen bonds in the molecule, and decreasing the energy loss during the desolvation of amide N—H under a hydrophobic environment in the cell membrane.

Meanwhile, the use of N-methyl amino acid result in the formation of an N-methyl peptide bond to be incorporated into the backbone of the peptide chain. 1) This structure, similar to a cyclic structure, is not easily identified or cleaved by proteases. 2) As an example, the incorporation of N-methyl peptide bonds improved cell membrane permeability and intestinal absorption resulting in increased bioavailability. 3) The double bond in a peptide bond allows the peptide bond to take both the cis-structure and the trans-structure, but the trans-structure is taken in conventional peptide bonds to avoid the high allylic strain of the cis-structure. However, the difference between the allylic strain of the cis-structure and that of the trans-structure in the N-methyl peptide bond is lower than that of conventional peptide bonds, so it occasionally takes a cis-structure. Thus, the structure of the entire peptide may change considerably by the insertion of one or more N-methyl peptide bonds to form a special structure that is not possible in normal peptides. It has thus been suggested that peptides that contain N-methyl peptide bonds can prove to be an effective library capable of binding to target protein surfaces, against which conventional peptides cannot provide a sufficient binding.

3. Methods for Synthesizing N-Methyl Peptides Using a Translation System, Constructing a Library of N-Methyl Peptides, and Searching for a Pharmaceutical Candidate Using Such Libraries Naturally-derived N-methyl peptides are synthesized by enzyme groups called non-ribosomal peptide synthetases (NRPS). These enzyme groups are extremely complicated, and no technology is currently established to create a peptide library by artificially tailoring these enzymes.

Several synthesis methods of N-methyl peptides that use translation systems to enable limit-free creation of N-methyl peptides have been reported thus far. Summarized below are studies on the N-methyl peptide translation synthesis that uses altered genetic codes created through artificially reassigning natural amino acids with N-methyl amino acids.

N-methylphenylalanine (Bain et al., Tehtahedron, 1991, 47, 2389-2400. Rabbit reticulocyte lysate), N-methylalanine (Ellman et al., Science, 1992, 255, 197-200. E. coli lysate), N-methylglycine (Chaung et al., Science, 1993, 259, 806-809. E. coli lysate), N-methyl aspartic acid (Karginov et al. JACS, 1997, 119, 8166-8176. Short et al., Biochemistry, 2000, 39, 8768-8781. Rabbit reticulocyte lysate) have been reported to be incorporated into one position of a peptide/protein using a UAG (terminator) codon.

In addition, a similar method using a sense codon have also been reported. Many such examples use a reconstituted cell-free translation system (reconstituted cell-free translation system; Y. Shimizu et al., Nature Biotechnology, 2001, vol. 19, p. 751-755, etc.) as a peptide expression system to avoid competition with natural amino acids.

Green et al. performed translation-synthesis of dipeptides using 20 types of N-methyl amino acids (Merryman et al., Chem. Biol., 2004, 11, 575-582. Reconstituted in vitro translation system. *E. coli*). The N-methyl aminoacyl tRNA was prepared according to the following three steps: 1) protecting the amino group with 2-nitrobenzaldehyde using aminoacyl-tRNA provided by the aminoacyl tRNA synthetase (ARS) as the substrate; 2) methylating the amino group with formaldehyde; 3) deprotecting 2-nitrobenzyl group by UV radiation. Szostak et al. successfully synthesized N-methyl peptides consisting of the following three N-methyl amino acids: N-methylvaline, N-methylleucine, N-methylthreonine (Subtelny et al., JACS, 2008, 130, 6131-6136, Reconstituted in vitro translation system. *E. coli*).

Cornish et al. successfully translationlly-synthesized a tripeptide by assigning N-methylalanine or N-methylphenylalanine to the GUU codon (valine) (Tan et al., JACS, 2004, 126, 12752-12753, Reconstituted in vitro translation system. *E. coli*).

Kawakami et al. successfully incorporated various N-methyl amino acids using Flexizyme, which is an RNA catalyst (ARS ribozyme) having an acyl tRNA synthetase-like activity (Kawakami et al., Chem. Biol., 2008, 15, 32-42. Reconstituted in vitro translation system. *E. coli*). They have successfully synthesized an N-methyl peptide comprising 10 continuous residues consisting of 3 types of N-methyl amino acids. Kawakami et al further translationally synthesized a cyclic peptide containing four N-methyl amino acids incorporated therein.

Typical ARS ribozymes are described in the following documents (H. Murakami, H. Saito, and H. Suga, (2003), Chemistry & Biology, Vol. 10, 655-662; H. Murakami, D. Kourouklis, and H. Suga, (2003), Chemistry & Biology, Vol. 10, 1077-1084; H. Murakami, A. Ohta, H. Ashigai, H. Suga (2006) Nature Methods 3, 357-359 "A highly flexible tRNA acylation method for non-natural polypeptide synthesis"; N. Niwa, Y. Yamagishi, H. Murakami, H. Suga (2009) Bioorganic & Medicinal Chemistry Letters 19, 3892-3894 "A flexizyme that selectively charges amino acids activated by a water-friendly leaving group"; and WO 2007/066627 "Multi-Purpose Acylation Catalayst and Use thereof").

On the other hand, only one example has been published so far concerning the construction of a peptide library consisting of N-methyl amino acids using a translation system and its application, which is a search for pharmaceutical agent candidates. Roberts et al. translation-synthesized an N-methyl peptide library consisting of N-methylphenylalanine assigned to the GUA codon (valine) and confirmed that such method is compatible with the mRNA display method (Frankel et al., Chem. Biol., 2003, 10, 1043-1050. tRNA-depleted rabbit reticulocyte lysate). Further, the same group reported a peptide cyclization method using a crosslinking agent (disuccinimidyl glutarate, DSG) and a mRNA display method that assigns N-methylphenylalanine to a UAG codon in the random NNS (wherein, N is one of A, R, C or G and S is C or G) region (Millward et al., ACS Chem. Biol. 2007, 2, 625-634. Rabbit reticulocyte lysate). As a result, a cyclic peptide binding to a target protein was obtained, however no N-methylphenylalanine was found in the selected peptide. It is not clear whether such result is due to the low quality (that is, the quality assurance of whether a peptide containing N-methylphenylalanine is included in the library) of the library constructed by Roberts et al. per se, or to the absence of N-methylphenylalanine in the active peptide, but the result clearly indicates that it is difficult to obtain biologically active species of the desired non-standard peptide containing N-methyl amino acids with the current maturity level of the given technology/methods.

As the above examples indicate, no peptide library has been created so far that contains more than a single N-methyl amino acid, nor has there been any successful selection or identification of such a peptide from such library(ies).

4. Preparation of Peptide Libraries Using In Vitro Display

In vitro display is a system that displays the phenotype with the genotype through conjugating a phenotype and a genotype, which encodes the sequence of the phenotype, by a noncovalent bond or a covalent bond and enables enrichment and amplification (selection) of active species using replication systems reconstituted in test tubes. The greatest advantage of the present system is that it allows one to search through a library encompassing a wide variety of nonstandard peptides, made possible by excluding prokaryote and eukaryote organisms from use as mediums, enabling the selection of highly active physiological substance (i.e. peptide herein). A typical comparative example is that of a phage display using *E. coli* as the replication medium, which enables a selection from a library with a diversity of 10 to the $7^{th}$ power. In comparison, an in vitro display enables one to search a library with a diversity of 10 to the $13^{th}$ power. In vitro display includes ribosome display, mRNA display, PD display (patented as RAPID display). Although mRNA display is explained below as an example, the library of non-standard peptide compounds disclosed in the present specification is applicable to all in vitro displays.

mRNA display is a technology in which the peptide is linked to its template mRNA, allowing the pairing of the amino acid sequence of a peptide with its nucleic acid sequence. To achieve such a complex, a puromycin, which is a terminal analog of acylated tRNA, is linked to the 3' terminal of mRNA via a suitable linker, and the linked product is added to the translation reaction to incorporate puromycin to site A of the ribosome and form a covalent bond of puromycin and a peptide in the process of elongation. Consequently, the translation product, that is the peptide molecule, remains conjugated to its template mRNA via the puromycin (Roberts et al., Proc. Natl. Acd. Sci. USA, 1997, 94, 12297-12302, Nemoto et al., FEBS Lett., 1997, 414, 405-408, JP 3683282 B (WO98/16636), JP 3683902 B, JP 3692542 B (WO98/31700)).

Peptide libraries having a variety of 10 to the $13^{th}$ power can be prepared by such in vitro display method, but the libraries reported thus far have been constituted of proteinogenic amino acids only. There is no known example of one successfully creating a library comprising genotypes that display peptides containing multiple special (non-standard) amino acids (including N-methyl amino acid) and cyclic structures, and performing selection therefrom.

5. HPV and Uterine Cervix Cancer

Among cancers specific to women, uterine cervix cancer is second only to breast cancer in the number of occurrences. There were 470,000 occurrences and 230,000 deaths reported worldwide annually, and 10,000 or more occurrences and 3,000 or more deaths reported in Japan annually. The prerequisite of developing uterine cervix cancer is Human papillomavirus (HPV) infection, especially high-risk (16, 18, 31, 33, 35, 39, 45, 51, 52, 56, 58, 59, 66, 68, 73-type) HPV infection. Then, after 10 to 30 years of latent infection, the cell goes through malignant transformation to develop uterine cervix cancer. However, uterine cervix cancer can be almost completely (100%) prevented by preventing HPV infection, and HPV vaccines, Cervarix (GlaxoSmithKline) and Gardasil (Merck), are used in at least 100 countries around the world, and approved in Japan since September 2009. Unfortunately, the vaccines are ineffective on virus carriers, and they are ineffective against HPV infections other than type 16 HPV and type 18 HPV, since the capsid proteins of those HPVs were used as antigens in the vaccines. There is thus a need for the development of a therapeutic agent to treat uterine cervix cancer.

Latent infection of HPV spreads through the replication of the HPV genome in HPV infected cells and their distribution to daughter cells. In the process, the HPV genomes are incorporated into the host genomes so that proteins encoded by the HPV initial gene group are expressed at a high level, and an intracellular environment that is advantageous to the replication of virus genomes appears. Matters considered particularly important are immortalization, growth promotion, and inactivation of the tumor suppressor gene caused by the virus proteins E6 and E7.

E7 is a protein consisting of about 100 amino acid residues, and consists of CR1 (conserved region 1) on the N terminal, CR2 and a zinc finger domain. It binds to an Rb family protein (pRb, p107, p130) via the LXCXE motif of CR2. Rb creates a complex with the transcription factor E2F, inactivates E2F and arrests the cell at the G0 phase. However, when E7 binds to Rb, E2F is freed and activated, and the cell cycle restarts. Further, E7 binds mutually to both pRb and μ-calpain to accelerate the decomposition of pRb.

E6 binds with ubiquitin ligase E6AP in the host cell via the LXXLL motif in E6 to promote the ubiquitination and decomposition of the cancer inhibitor p53. p53 arrests the cell cycle at the G1 phase, and induces recovery when the DNA is damaged and induces apoptosis when the damage is great. When E7 inactivates Rb family proteins and moves the cell cycle forward, apoptosis is induced via p53. E6 prevents apoptosis and promotes virus growth by inhibiting the above growth arrestive effects of p53. In addition, the E6-E6AP complex promotes the ubiquitination and decomposition of a protein group and a telomerase inhibitor NFX1, the protein group having a PDZ domain that is responsible for maintaining cell polarity and controlling cell growth; accordingly, the E6-E6AP complex works in various ways to induce cancer conversion/proliferation. Chromosomes of currently available uterine cervix cancer cells, namely, HeLa cells, SiHa cells, and Caski cells, respectively include HPV18, HPV16, HPV16 genomes, which induces high expression of E6. It is observed that p53 is accumulated and apoptosis is induced when E6 or E6AP is knocked down by siRNA, indicating that the effects of E6 depend on E6AP.

6. Ubiquitin Ligase E6AP

The ubiquitin ligase E6AP (E6 associated protein, 852 amino acid residues), encoded by the UBE3A gene was discovered in 1990 by its function to bind to the cancer inhibitor p53 via E6, promoting its ubiquitination and decomposition using the 26S proteasome. The C terminal domain of E6AP, consisting of about 350 amino acid residues, is called the HECT (Homologous to E6AP Carboxyl-Terminus) domain, and forms a large family of ubiquitin E3 ligases. About 50 types of ubiquitin ligases contain a HECT domain have been confirmed in human and 5 types have been confirmed in yeast. The HECT domain includes a a large N terminal lobe (about 250 amino acid residues) and a C terminal lobe (about 100 amino acid residues) linked by a short hinge section, and in the C terminal lobe, there exists an activation cysteine. The activation E2 protein that has be ubiquitinated binds to the N terminal lobe in the HECT domain to transfer the ubiquitin to the cysteine in the C terminal lobe and forms a ubiquitin thioester intermediate. Subsequently, the amino group on the lysine side chain of the target protein recruited by the domain upstream of the HECT domain forms an isopeptide bond with the ubiquitin on the HECT to ubiquitinate the target. In former studies, E6 was bound to the α-helix consisting of 18 amino acids that are upstream of the HECT domain of E6AP by about 120 amino acid residues to form an E6-E6AP complex. The complex binds with p53 to poly-ubiquitinate p53, and induces decomposition.

Thus far there are no inhibitors of ubiquitin ligase E6AP that have been investigated as therapeutic agents for the treatment of uterine cervix cancer. In addition, there are no inhibitors of ubiquitin ligase E6AP specifically targeting the HECT domain. Furthermore, it can be predicted that agents targeting human-derived E6AP could represent a novel therapeutics class against various high-risk HPV-derived uterine cervix cancers.

CITATION LIST

Patent Documents

Patent Document 1: WO 2007/066627
Patent Document 2: Japanese Patent No. 3683282
Patent Document 3: Japanese Patent No. 3683902
Patent Document 4: Japanese Patent No. 3692542

Non-Patent Document

Non-patent Document 1: Bain et al., Tehtahedron, 1991, 47, 2389-2400.
Non-patent Document 2: Ellman et al., Science, 1992, 255, 197-200.
Non-patent Document 3: Chaung et al., Science, 1993, 259, 806-809.
Non-patent Document 4: Karginov et al. JACS, 1997, 119, 8166-8176.
Non-patent Document 5: Short et al., Biochemistry, 2000, 39, 8768-8781.
Non-patent Document 6: Merryman et al., Chem. Biol., 2004, 11, 575-582.
Non-patent Document 7: Subtelny et al., JACS, 2008, 130, 6131-6136.
Non-patent Document 8: Tan et al., JACS, 2004, 126, 12752-12753.
Non-patent Document 9: Frankel et al., Chem. Biol., 2003, 10, 1043-1050.
Non-patent Document 10: Millward et al., ACS Chem. Biol., 2007, 2, 625-634.
Non-patent Document 11: Kawakami et al., Chem. Biol., 2008, 15, 32-42.
Non-patent Document 12: Y. Shimizu et al., Nature Biotechnology, 2001, vol. 19, p. 751-755
Non-patent Document 13: H. Murakami, H. Saito, and H. Suga, (2003), Chemistry & Biology, Vol. 10, 655-662
Non-patent Document 14: H. Murakami, D. Kourouklis, and H. Suga, (2003), Chemistry & Biology, Vol. 10, 1077-1084
Non-patent Document 15: H. Murakami, A. Ohta, H. Ashigai, H. Suga (2006) Nature Methods 3, 357-359
Non-patent Document 16: N. Niwa, Y. Yamagishi, H. Murakami, H. Suga (2009) Bioorganic & Medicinal Chemistry Letters 19, 3892-3894
Non-patent Document 17: Roberts et al., Proc. Natl. Acd. Sci. USA, 1997, 94, 12297-12302, Non-patent Document 18: Nemoto et al., FEBS Lett., 1997, 414, 405-408

SUMMARY OF INVENTION

Technical Problem

Non-standard peptides consisting of a macrocyclic structure or containing special (non-standard) amino acid(s) are receiving attention as new drug development seeds, since they often exhibit excellent membrane permeability, target binding capacity and in vivo stability. However, peptide libraries have been primarily restricted to natural linear or disulfide linked peptides; accordingly, such libraries lack sufficient variety and properties, severely limiting the identification of new pharmaceutical agents.

The present inventors possess a technology of constructing a non-standard peptide through translation-synthesis. Further, the present inventors possess a technology of peptide cyclization using an intramolecular specific reaction to create non-reducible cyclic non-standard peptides produced by translational-synthesis.

The object of the present invention is to construct a peptide library of non-standard peptide compounds using a cell-free (in vitro) translation system, using one of the above two technologies singly or in combination, and further to establish a technology for screening a non-standard peptide compound to bind to the target protein using an in vitro display method.

Solution to Problem

The present inventors established a technology for screening a non-standard peptide aptamer having a high binding affinity against a target substance by using genetic code reassignment technology, constructing a non-standard peptide library containing multiple special (non-standard) amino acids and combining the library with a display system.

Specifically, the present inventors constructed a cyclic non-standard peptide library containing multiple N-methyl amino acids using N-methyl amino acids as an example of a special (non-standard) amino acid to be incorporated in the random sequence of the non-standard peptide library. Ubiquitin ligase E6AP was used as an example of a target, and a cyclic N-methyl peptide having a high specificity to the target was successfully obtained.

A brief summary of the invention is as follows.

(1) A method for selecting a non-standard peptide that binds to a target substance from a peptide library, the method comprising the steps of:
(i) preparing a peptide library comprising non-standard peptides wherein special (non-standard) amino acids are randomly incorporated into the peptide sequence by an in vitro translation system comprising tRNAs each acylated with a special (non-standard) amino acid;
(ii) bringing the peptide library in contact with a target substance;
(iii) selecting a non-standard peptide that binds to the target substance, wherein, in step (i), each peptide constituting the library is translated from a nucleic acid sequence encoding that peptide, and the nucleic acid sequence and its translation product, which is the peptide, are linked, and
a region encoding the peptide in the nucleic acid sequence includes a random sequence consisting of a repetition of different triplets, and at least some of the triplets in the random sequence correspond to (artificial) codons that specify special (non-standard) amino acids.

(2) The method according to (1), wherein the step (i) comprises acylating tRNA with a special (non-standard) amino acid using an RNA catalyst characterized by an acyl-tRNA synthetase-like activity.

(3) The above method, wherein the tRNA acylated by a special (non-standard) amino acid is a tRNA prepared by in vitro transcription.

(4) The method according to (1), wherein the step (i) comprises preparing a library of mRNAs that each include a region encoding a peptide, and translating the mRNAs.

(5) The method according to (1), wherein the region encoding the peptide further includes sequences corresponding to
a codon specifying an amino acid having Functional Group 1, and
a codon specifying an amino acid having Functional Group 2, and
Functional Group 1 and Functional Group 2 are a pair of functional groups that are capable of bond forming reaction, and in the step (i), cyclic special peptides are included in the library by the special (non-standard) amino acid being incorporated in the peptide sequence by a pairing of an anticodon of tRNA acylated by a special (non-standard) amino acid and an artificial codon specifying the special (non-standard) amino acid, and the translation products, which are the peptides, being cyclized by a bond forming reaction between Functional Group 1 and Functional Group 2.

(6) The method according to (1), wherein each triplet constituting the random sequence is selected from codons having the following sequences:
an $N^1N^2U$ codon {wherein $N^1$ and $N^2$ are independently one of A, U, C or G};
an $N^1N^2K$ codon {wherein $N^1$ and $N^2$ are independently one of A, U, C or G, and K is either C or G};
an $N^1N^2N^3$ codon {wherein $N^1$, $N^2$ and $N^3$ are independently one of A, U, C or G}.

(7) The method according to (6), wherein the random sequence consists of 2 or more repetitions of one of the $N^1N^2U$ codon, the $N^1N^2K$ codon and the $N^1N^2N^3$ codon.

(8) The method according to (5), wherein Functional Group 1 and Functional Group 2 are one of (A) to (C) below, which are pairs of functional groups:

[Formula 1]

(A)

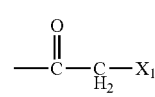
(A-1)

(A-2)

(B)

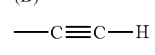
(B-1)

(B-2)

(C)

(C-1)

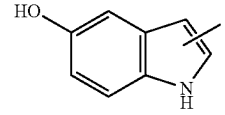
(C-2)

(wherein, $X_1$ is either Cl or Br, and Ar is an aromatic ring that can comprise a substituent).

(9) The method according to (5), wherein the amino acid having Functional Group 1 is an amino acid having a chloroacetyl group and the amino acid having Functional Group 2 is cysteine.

(10) The above method, wherein the region encoding the peptide comprises (a) to (c) below:
(a) an initiator codon specifying an amino acid having a chloroacetyl group,
(b) a random sequence consisting of repetitions of an NNU {wherein, N is one ribonucleotide of A, U, C or G} codon, which comprises one or more artificial codons specifying special (non-standard) amino acids, and
(c) a codon specifying cysteine,
wherein the amino acid having a chloroacetyl group is incorporated at the N terminal of the peptide by the pairing of the initiator codon with an anticodon of an initiator tRNA acylated by the amino acid having a chloroacetyl group,
and one or more special (non-standard) amino acid are incorporated in a peptide by pairing of each artificial codon specifying a special (non-standard) amino acid in the random sequence and an anticodon of an elongator tRNA acylated by a special (non-standard) amino acid, and the translation products, which are the peptides, are cyclized by a bond forming reaction between the chloroacetyl group and a sulfhydryl group of cysteine.

(11) The above method, wherein the in vitro display library is a library selected from a group consisting of either ribosome display library, mRNA display library, RAPID display library, or PD display library.

(12) The method according to (1), wherein the step (iii) includes sequencing a nucleic acid coding for a cyclic non-standard peptide bound to a target substance.

(13) An in vitro display library comprising complexes of mRNAs and their translation products, which are cyclic special (non-standard) amino acids, obtainable by translating an mRNA library with a peptide coding region comprising:
(a) an artificial codon specifying an amino acid having a chloroacetyl group,
(b) a random sequence consisting of a repetition of different triplets, which comprises one or more artificial codons each specifying a special (non-standard) amino acid, and
(c) a codon specifying cysteine, using a reconstituted in vitro translation system comprising at least:
(d) an artificial tRNA having an anticodon complementary to the codon of (a), and acylated with the amino acid having a chloroacetyl group,
(e) at least one artificial tRNA acylated by a special (non-standard) amino acid, and
(f) a cysteine, a cysteine tRNA, and a cysteinylRS (CysRS).

(14) A kit for preparing an in vitro display library comprising complexes of cyclic non-standard peptides and nucleic amino acid sequences encoding said peptides comprising at least,
(i) an mRNA comprising (a) to (c) below, as a peptide encoding region:
(a) an artificial codon specifying an amino acid having a chloroacetyl group,
(b) a random sequence consisting of a repetition of different triplets, which comprises artificial codons each specifying a special (non-standard) amino acid, and
(c) a codon specifying cysteine, and
(ii) (d) to (e) below, which are aminoacyl tRNAs:
(d) an artificial initiator tRNA having an anticodon complementary to the codon of (a), and acylated with the amino acid having a chloroacetyl group,
(e) artificial elongator tRNAs each having an anticodon complementary to the artificial codon of (b), and acylated by different special (non-standard) amino acids, and
(iii) a cysteine and a tRNA acylated by cysteine, and
(iv) an isolated ribosome.

(15) The above method, wherein the special (non-standard) amino acid is an N-methyl amino acid.

(16) The method according to (1), wherein the target substance is ubiquitin ligase E6AP.

(17) A compound MCP11, which is Cyclo(-Ac-$^D$WCDV$^{Me}$SGR$^{Me}$F$^{Me}$GY$^{Me}$FPC)G-OH obtained by the method of (16)

Advantageous Effect of Invention

A non-standard peptide library can be constructed by using the technology of constructing non-standard peptides by translation-synthesis and/or the peptide cyclization technology. Further, a combination of the characteristics of the two technologies enables the construction of a cyclic non-standard peptide library that includes special (non-standard) amino acids such as N-methyl amino acids.

The establishment of the translation-synthesis technology of a cyclic non-standard peptide library containing special (non-standard) amino acids and the technology of combining the former technology with a display system made it possible to quickly and inexpensively search and identify highly-active cyclic non-standard peptides having protease resistance.

BRIEF DESCRIPTION OF DRAWINGS

FIG. 2-1 shows the preparation of N-methyl amino acid-tRNA. (Example 2)

FIG. 2-2 shows the preparation of D-$^{ClAc}$W-tRNA. (Example 2)

FIG. 5-1 shows the progress of the selection. (Example 4)

FIG. 5-2 shows an analysis of the peptide sequence through the DNA sequence, (Example 5)

FIG. 5-3 shows the translation-synthesis and the confirmation of the binding of MCP11. (Example 5)

FIG. 5-4 shows the affinity analysis result of MCP11 and the derivative using the surface Plasmon resonance method. Biotinylated E6AP-HECT was fixed to the streptavidin chip to analyze affinity using the peptides. (Example 7)

DESCRIPTION OF EMBODIMENTS

Figure 1:
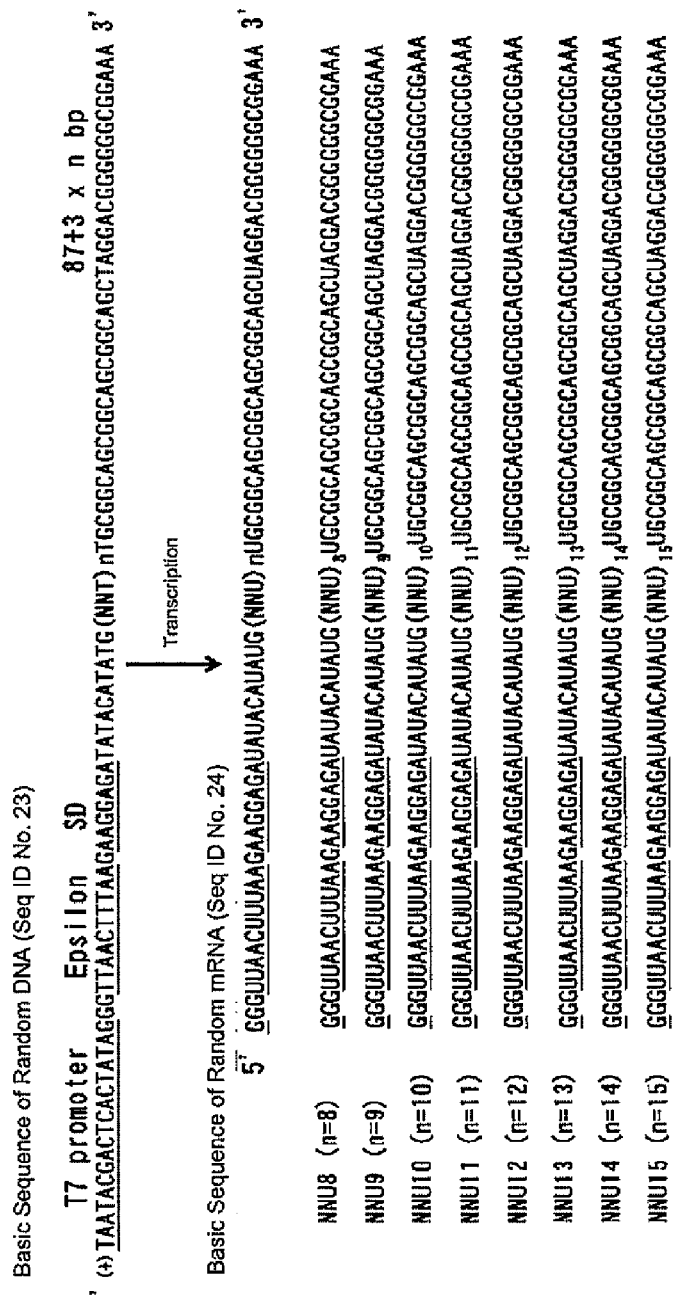
FIG. 1 shows the preparation of random mRNA whose length is $(NNU)_n$ (n is 2 or larger). (Example 1)

The present invention relates to a method for screening a non-standard peptide compound in a peptide library that binds to the target substance, comprising the following steps:
(i) preparing a library comprising non-standard peptides wherein special (non-standard) amino acids are randomly incorporated in the peptide sequence by an in vitro translation system comprising tRNAs each acylated by a special (non-standard) amino acid; (ii) bringing the obtained peptide library in contact with a target substance; and (iii) selecting a non-standard peptide that binds to the target substance.

A peptide library is a population of various types of peptides; screening is the act of selecting the peptide with the desired function from the population. The present invention constructs a library of non-standard peptides each containing multiple special (non-standard) amino acids using the genetic code reprogramming technology, and screens a peptide aptamer that has high binding capacity to the target protein, by combining the library with an in vitro display system. Hence, the above step (i) includes preparing a library consisting of nucleic acids that encodes the peptides, translating the codes, and conjugating the nucleic acids with their cognate translation products to construct a library in which the phenotype (amino acid sequence of the peptide) is displayed linked to its' genotype (nucleic acid sequence).

Reprogramming of the Genetic Code

Reprogramming of the genetic code is to artificially assign special (non-standard) amino acids to existing codons. Special (non-standard) amino acids include all the amino acids that have structures differing from the 20 proteinogenic amino acids used in natural translation, which can be artificially produced or which can exist in nature. That is, non-proteinogenic amino acid or artificial amino acid, created by chemically changing or modifying part of the side chain structure of proteinogenic amino acid, D-amino acid, N-methyl amino acid, N-acyl amino acid, β-amino acid, amino acid derivatives having a structure in which the amino group or the carboxyl group on the amino acid backbone is substituted, and the like are all included. N-methyl amino acid is a special (non-standard) amino acid in which a methyl group is incorporated into the α-amino group of the amino acid.

In a natural translation, an alignment of three bases (triplet) on an mRNA acts as a single codon specifying one proteinogenic amino acid, and a peptide corresponding to that alignment is synthesized. The linkage of the codon and the amino acid is performed according to the following 2 steps: (i) a terminal end of tRNA is conjugated with a corresponding amino acid by an aminoacyl tRNA synthetase (ARS); (ii) the tRNA anticodon is paired with the corresponding codon of an mRNA, causing polymerization of amino acids on the tRNA based on the mRNA information to synthesize a peptide.

The above linkages between codons and anticodons are determined with near universality, and one of the 20 types of proteinogenic amino acids is assigned to each of the 64 types of codons. However, the genetic code can be reprogrammed by using a reconstituted translation system and an artificially aminoacyl RNA catalyst flexizyme.

A reconstituted translation system is a translation system created by isolating, refining and mixing factors involved in the translation-synthesis of proteins or peptides, such as a ribosome, translation factors, tRNAs, amino acids and energy sources including ATP and GTP. For example, a system using the ribosome of *E. coli*, as shown in the following documents, is known in the art: H. F. Kung, B. Redfield, B. V. Treadwell, B. Eskin, C. Spears and H. Weissbach (1977) "DNA-directed in vitro synthesis of beta-galactosidase. Studies with purified factors" The Journal of Biological Chemistry Vol. 252, No. 19, 6889-6894; M. C. Gonza, C. Cunningham and R. M. Green (1985) "Isolation and point of action of a factor from *Escherichia coli* required to reconstruct translation" Proceeding of National Academy of Sciences of the United States of America Vol. 82, 1648-1652+ M. Y. Pavlov and M. Ehrenberg (1996) "Rate of translation of natural mRNAs in an optimized in Vitro system" Archives of Biochemistry and Biophysics Vol. 328, No. 1, 9-16; Y. Shimizu, A. Inoue, Y. Tomari, T. Suzuki, T. Yokogawa, K. Nishikawa and T. Ueda (2001) "Cell-free translation reconstituted with purified components" Nature Biotechnology Vol. 19, No. 8, 751-755; H. Ohashi, Y. Shimizu, B. W. Ying, and T. Ueda (2007) "Efficient protein selection based on ribosome display system with purified components" Biochemical and Biophysical Research Communications Vol. 352, No. 1, 270-276.

Meanwhile, a flexizyme is an artificial RNA catalyst that can conjugate any amino acid or hydroxyl acid to any tRNA. Examples of known art are provided below: H. Murakami, H. Saito, and H. Suga, (2003), Chemistry & Biology, Vol. 10, 655-662; H. Murakami, D. Kourouklis, and H. Suga, (2003), Chemistry & Biology, Vol. 10, 1077-1084; H. Murakami, A. Ohta, H. Ashigai, H. Suga (2006) Nature Methods 3, 357-359 "The flexizyme system: a highly flexible tRNA aminoacylation tool for the synthesis of nonnatural peptides"; N. Niwa, Y. Yamagishi, H. Murakami, H. Suga (2009) Bioorganic & Medicinal Chemistry Letters 19, 3892-3894 "A flexizyme that selectively charges amino acids activated by a water-friendly leaving group"; and WO 2007/066627 "Multi-Purpose Acylation Catalayst and Use thereof". A flexizyme is also known as the original flexizyme (Fx), and modifications thereof, namely, dinitrobenzyl flexizyme (dFx), enhanced flexizyme (eFx), and aminoflexizyme (aFx).

The translation system used for reprogramming genetic codes is constructed by freely removing the component factor of the translation system depending on the purpose, and reconstituting just the necessary ingredients. For example, a translation system may be reconstituted after removing one or more given amino acids, and the condons corresponding to the removed amino acids become vacant condons. Subsequently, a flexizyme may be used to conjugate special (non-standard) amino acids with tRNAs each having an anticodon that is complementary to the respective vacant codons, and the conjugated product is added to the translation. Through the above process, special (non-standard) amino acids are assigned to the above mentioned codons to be translated into peptides that incorporate special (non-standard) amino acids in place of the removed amino acids.

Alternatively, a codon corresponding to a given amino acid can be vacated by not using the naturally-derived cognate tRNA corresponding to the given amino acid. For example, a suppressor tRNA synthesized in vitro that has no modified base and that is conjugated with a special (non-standard) amino acid can be used in place of a naturally-derived tRNA that corresponds to multiple codons so that the codon corresponding to the suppressor tRNA is reprogrammed as an artificial codon for the special (non-standard) amino acid. In the present specification, tRNA refers to both a natural tRNA and an artificially constructed tRNA (artificial tRNA). A typical example of an artificial tRNA is a tRNA prepared by in vitro transcription using an appropriate RNA polymerase, such as T7 polymerase.

The reprogramming of the genetic code enables the translation-synthesis of various non-standard peptides as in vitro translation products based on mRNA templates of appropriate sequences. Non-standard peptides include various translation products that can be synthesized by a system that combines a flexizyme and a reconstituted translation system. The use of flexizymes enables tRNA to be acylated by not just the 20 types of natural proteinogenic amino acids, but also amino acids with various side chains, β-amino acid, γ-amino acid and δ-amino acid, D-amino acid, and amino acid derivatives having a structure in which the amino group or the carboxyl group on the amino acid backbone is substituted. Hence, the meaning of a non-standard peptide includes polymers that comprise these various substrates as components. In addition, non-standard peptides can have a main chain with a structure differing from a normal amide bond. Examples of non-standard peptides include depsipeptide constituted from an amino acid and a hydroxyl acid, polyester which is a continuous condensation of hydroxyl acids, N-methyl peptides, and peptides having various acyl groups (e.g. acetyl groups, pyroglutamic acids, fatty acids) on the N-terminal.

The Examples of the present application specifically describes an N-methyl peptide obtained by reassigning one or more N-methyl amino acids to the artificial codons using the genetic code reprogramming technology. N-methyl peptide is the collective term indicating peptides comprising one or more N-methyl amino acids. The N-methyl peptide incorporates an N-methyl peptide bond, which is a peptide bond (—NHCO—) in the peptide main chain methylated at the nitrogen part, as a result of containing an amino acid whose α-amino group is methylated.

The Kawakami et al. article mentioned in the PRIOR ART section above showed that N-methyl amino acid can be assigned to the existing codon by genetic-code reprogramming to incorporate N-methylglycine, N-methylalanine, N-methylserine, N-methylthreonine, N-methylcysteine, N-methylmethionine, N-methylglutamine, N-methylhistidine, N-methylphenylalanine, N-methyltyrosine, N-methyltryptophan, N-methylnorvaline, N-methylnorleucine, N-methyl-p-nitrophenylalanine, N-methyl-p-methoxyphenylalanine in the peptide as an N-methyl amino acid. The same N-methyl amino acid can be used in the present invention.

Artificial Codons

In a naturally occurring translation, one of the 20 types of proteinogenic amino acids and a translation terminator is assigned to each of the 64 types of codons according to the universal genetic code table shown below.

(A) and thymine (T), and guanine (G) and cytosine (C) form pairs in the DNA; A and uracil (U), and G and C form pairs in the RNA. Further, non-Watson-Crick base pairs such as G-A and G-U exist in RNAs as thermodynamically stable base pairs, so these combinations are also referred to as complementary in the present specification.

Described below as an example is the relationship between the artificial codon and the anticodon used in the present Examples. For example, the codon of $^{Me}$Ala is 5'-GCU-3' and the anticodon of tRNA which forms a complete complementary chain is 3'-CGA-5'. The anticodon will be written as 5'-AGC-3', since it is commonly written from the base on the 5' side. Further, pairs other than Watson-Crick base pairs, such as a pair of U and G, is acceptable in the complementary chain formed by the third base on the 3' side of the codon and the first base on the 5' side of the anticodon according to the Wobble rule. Accordingly, the $^{Me}$Ala codon 5'-GCU-3' can be correctly read by the tRNA anticodon 5'-GGC-3'.

The present invention allows the initiator codon to be rewritten, in addition to the codon used in the peptide chain elongation reaction. The initiator codon is a codon indicating where translation initiates and encoding an initiator amino acid that becomes the N terminal of the peptide on the mRNA. To initiate translation of the mRNA, a specific tRNA called the initiator tRNA is required. Translation is initiated by the initiator tRNA binding to a small subunit of ribosome, with an initiation factor (IF), and the small initiation subunit of ribosome binding to the initiator codon on the mRNA. An initiator tRNA comprises an anticodon corresponding to an initiator

TABLE 1

| Base of the first letter | Base of the second letter | | | | | | | |
|---|---|---|---|---|---|---|---|---|
| | U | | C | | A | | G | |
| | codon | amino acid | codon | amino acid | codon | amino acid | codon | amino acid |
| U | UUU | phenylalanine | UCU | serine | UAU | tyrosine | UGU | cysteine | U
| | UUC | phenylalanine | UCC | serine | UAC | tyrosine | UGC | cysteine | C
| | UUA | leucine | UCA | serine | UAA | terminator | UGA | terminator | A
| | UUG | leucine | UCG | serine | UAG | terminator | UGG | tryptophan | G
| C | CUU | leucine | CCU | proline | CAU | histidine | CGU | arginine | U
| | CUC | leucine | CCC | proline | CAC | histidine | CGC | arginine | C
| | CUA | leucine | CCA | proline | CAA | glutamine | CGA | arginine | A
| | CUG | leucine | CCG | proline | CAG | glutamine | CGG | arginine | G
| A | AUU | isoleucine | ACU | threonine | AAU | asparagine | AGU | serine | U
| | AUC | isoleucine | ACC | threonine | AAC | asparagine | AGC | serine | C
| | AUA | isoleucine | ACA | threonine | AAA | lycine | AGA | arginine | A
| | AUG | methionine | ACG | threonine | AAG | lycine | AGG | arginine | G
| G | GUU | valine | GCU | alanine | GAU | aspartic acid | GGU | glycine | U
| | GUC | valine | GCC | alanine | GAC | aspartic acid | GGC | glycine | C
| | GUA | valine | GCA | alanine | GAA | glutamic acid | GGA | glycine | A
| | GUG | valine | GCG | alanine | GAG | glutamic acid | GGG | glycine | G In contrast, codons rewritten by the genetic code reprogramming and encoding special (non-standard) amino acids that differ from the existing genetic codes in the universal code table are referred to as artificial codons.

The relationship between codons and anticodons depend on the pairing of complementary bases. The pairing of an anticodon of tRNA conjugated with a special (non-standard) amino acid and an artificial codon on the mRNA specifying a special (non-standard) amino acid in the translation reaction on the ribosome leads to the incorporation of a special (non-standard) amino acid into the peptide chain.

A pairing of bases is the act of forming a base pair through hydrogen bonding of two predetermined bases from among the bases of nucleic acid. The combination of bases that can form a base pair are "complementary" to each other. Adenine codon, and recognizes the initiator codon. Since AUG, which is generally a codon of methionine, is used as the initiator codon in the universal code table, the initiator tRNA includes an anticodon corresponding to methionine, and the initiator tRNA always carries methionine (formylmethionine for a prokaryotic cell). However, the initiator amino acid does not need to be limited to methionine when the genetic code reprogramming is used. That is, any amino acid that is not methionine can be bound to the initiator tRNA to initiate translation. Further, the initiator codon is also not limited to AUG when any initiator amino acid binds to an initiator tRNA replaced by any anticodon using a flexizyme. That is, other artificial codons can be assigned as an initiator codon.

Cyclization of Peptides

Peptide is cyclized in the present invention by using the intracellular specific reaction of the non-cyclic non-standard peptide formed by translation-synthesis. The cyclization of peptide is performed by steps (i) and (ii) below:

(i) synthesizing non-cyclic peptide compounds comprising Functional Group 1 and Functional Group 2 as a pair of functional groups that can induce a bond forming reaction; and (ii) cyclizing a non-cyclic peptide compound by the bond forming reaction of Functional Group 1 and Functional Group 2.

A pair of functional groups that can induce a bond forming reaction is a pair of functional groups that are capable of a bond forming reaction between the pair of functional groups, namely Functional Group 1 and Functional Group 2, and that consequently changes a non-cyclic peptide compound to a cyclic peptide compound. Such pair of functional groups can be any pair of functional groups that can induce a bond forming reaction, without limitation. Additionally, the manner of reaction between the functional groups is not limited, and it can include various manners of reactions, such as a substitution reaction, an addition reaction, a condensation reaction and a cyclization-addition reaction; further, the manner (single bond, double bond and triple bond, etc.) and number of bonds formed in the reaction are not limited either.

Examples of a pair of functional groups include a pair of —$CH_2$-L (wherein, L is a leaving group such as —Cl, —Br and —$OSO_2CH_3$) and a nucleophile function group (—OH, —$NH_2$ and —SH, etc). An example of the bond forming reaction of Functional Group 1 and Functional Group 2 is the forming of a cyclic structure through the disulfide bond of two cysteine residues. However, a disulfide bond is easily reduced in vivo. Thus, the bond between Functional Group 1 and Functional Group 2 should preferably be a nonreducing bond to form a stable cyclic structure. The present inventors previously developed and reported a technology to cyclize a translated straight-chain peptide by a nonreducing bond (Goto et al., ACS Chem. Biol., 2008, 3, 120-129, WO 2008/117833 "Process For Synthesizing Cyclic Peptide Compound"). Such method can be used in the present application as well. A non-cyclic peptide compound is a non-cyclic compound encompassed in the above non-standard peptide, and it is the same thing as a linear peptide.

An example of a preferable pair of Functional Group 1 and Functional Group 2 that can be used in the present invention is shown below.

[Formula 2]

(A)

(A-1)

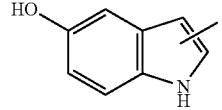

(B)

(A-2)

HS—

(B-1)

—C≡C—H (B-2)

$N_3$—

(C)

(C-1)

(wherein, $X_1$ is Cl or Br, and Ar is an aromatic ring that can include a substituent).

Examples of substituents of Ar include a hydroxyl group, a halogen atom, an alkyl group of 1 to 6 carbon atoms, an alkoxy group of 1 to 6 carbon atoms, a phenyl group, a phenoxy group, a cyano group and a nitro group, without limitation.

Pair (A) can provide the structure of formula (A-3) by the substitution reaction between functional groups. Pairs (B) and (C) can respectively provide structures (B-3) and (C-3) by the cyclization reaction between functional groups.

[Formula 3]

(A-3)

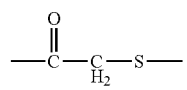

(B-3)

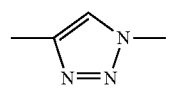

(C-3)

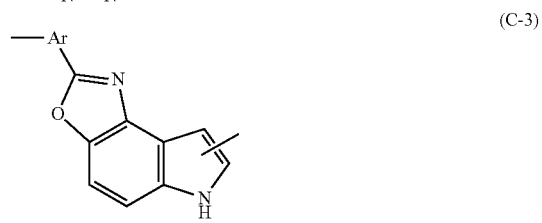

Assuming that an element (typically, an amino acid) that constitutes a non-cyclic peptide compound is one unit, the pair of functional groups needs to exist on units of different components, since the bonding of the two paired functional groups, existing in the non-cyclic peptide compound, forms a ring. The component will be called an amino acid compound and the unit of the component will be called an amino acid compound unit, for the sake of explanation. That is, the non-cyclic peptide compound is a compound possessing a pair of functional groups on different amino acid units. It is preferable for at least one amino acid compound unit to exist between an amino acid compound unit comprising one functional group and an amino acid compound unit comprising another functional group in the non-cyclic peptide compound; preferably, the amino acid compound units should exist in a number of 1 to 20, or 2 to 10, or 3 to 5 amino acid compound units.

A non-cyclic peptide compound comprising a pair of functional groups described above is synthesized by a translation-synthesis using an in vitro translation system in the present invention. When the amino acid comprising the functional groups for cyclization is a special (non-standard) amino acid and not a proteinogenic amino acid, it is incorporated into the peptide chain using a genetic code reprogramming technology.

In the first aspect of the invention, the translation-synthesis of the non-cyclic peptide compound is performed by a method comprising the steps of: providing (a) an initiator tRNA aminoacylated by an amino acid containing Functional Group 1, (b) an in vitro translation system that includes at least an amino acid containing Functional Group 2 and a tRNA aminoacylated by the amino acid, (c) a mRNA having a codon corresponding to the anticodon of the initiator tRNA and a codon corresponding to the anticodon of tRNA aminoacylated by an amino acid containing the Functional Group 2 at desired positions; and synthesizing a non-cyclic peptide compound by adding the aminoacylated initiator tRNA of (a) above and mRNA of (c) above to the in vitro translation system of (b) above.

In the non-cyclic peptide compound obtained by the method of the first aspect, the translation is initiated by the special (non-standard) amino acid containing Functional Group 1, and Functional Group 2 exists on the proteinogenic amino acid residue that is incorporated during the peptide chain elongation reaction.

Functional Group 1 can exist as a substituent on a carbon atom in the amino acid, such as α-carbon and β-carbon, or it can exist on such substituent on the carbon atom. In addition, Functional Group 1 can exist as a substituent on the nitrogen atom of the amino group, or it can exist on such substituent on the nitrogen atom of the amino group. Functional Group 1 needs to induce a bonding reaction with Functional Group 2. As explained below, Functional Group 1 should preferably be a functional group containing an appropriate leaving group, for example, a group of —CH$_2$-L (wherein, L is a leaving group, such as —Cl, —Br and —OSO$_2$CH$_3$), since Functional Group 2 is basically a nucleophilic functional group (—SH, —COOH and —OH, etc.) contained in cysteine, tyrosine and the like.

The special (non-standard) amino acid containing Functional Group 1 should preferably be, for example, an amino, acid compound containing the (A-1) group above on the nitrogen atom of the amino group. A specific example of the amino acid compound includes, for example, the compound of formula (1):

[Formula 4]

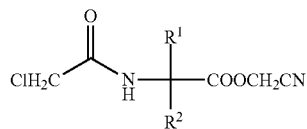

(1)

(wherein, R$^1$ and R$^2$ are each a hydrogen atom or an optional substituent conjugated to the carbon atom at position-α by carbon. Specifically, R$^1$ and R$^2$ are preferably one of the substituents on the α-carbon of the 20 types of proteinogenic amino acids. Further, R$^1$ and R$^2$ are preferably one of the combinations of substituents on the α-carbon of the proteinogenic amino acids. Specific examples of the compound of formula (1) include formula (1-1):

[Formula 5]

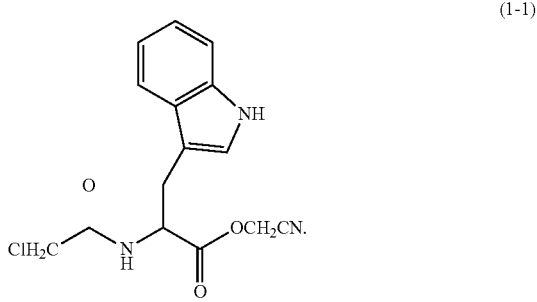

(1-1)

Amino acids comprising Functional Group 2 include cysteine, aspartic acid, glutamine and tyrosine. That is, Functional Group 2 is —OH, —SH, —C(=O)NH$_2$ and —COOH. Cysteine is preferable as an amino acid containing Functional Group 2. The amino acid containing Functional Group 2 is incorporated by a peptide chain elongation reaction in the reconstituted translation system comprising at least the amino acid and a corresponding tRNA.

In another method, which is the second aspect for synthesizing a cyclic peptide compound, both the amino acid containing Functional Group 1 and the amino acid containing Functional Group 2 are special (non-standard) amino acids. Functional Group 1 and Functional Group 2 can exist on a substituent on the nitrogen atom of the amino group or on a substituent on the carbon atom, such as α-carbon and β-carbon.

When the functional groups exist on the nitrogen atom, they can be incorporated on to the nitrogen atom of the amino acid amino group as an acyl substituent of the following formulae (20) to (24):

[Formula 6]

(20)

(21)

(22)

(23)

(24)

(wherein, n is an integer of 1 or higher, for example, 1 to 10, X$_1$ is the same as explained above) or a part of such acyl substituent.

When the functional groups exist on the α-carbon and the β-carbon, they can be incorporated as groups of formulae (25) to (30):

[Formula 7]

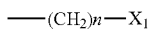  (25)

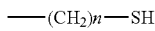  (26)

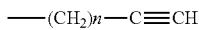  (27)

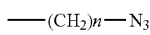  (28)

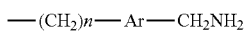  (29)

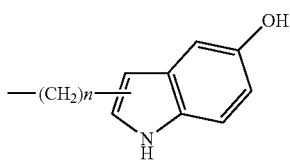  (30)

(wherein, n is an integer of 1 or higher, for example, 1 to 10, $X_1$ is the same as explained above).

Specific examples of amino acid compounds containing Functional Group 1 include, for example, a compound of formula (2), and specific examples of amino acid compounds containing Functional Group 2 include, for example, a compound of formula (3):

[Formula 8]

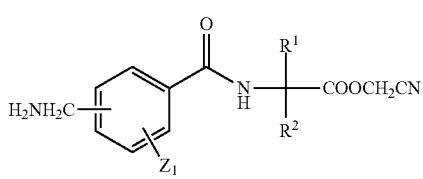  (2)

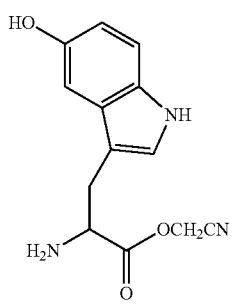  (3)

(wherein, $R^1$ and $R^2$ are the same as described above and $Z_1$ is an optional substituent. Z1 can be a hydroxyl group, a halogen atom, an alkyl group of 1 to 6 carbon atoms, an alkoxy group of 1 to 6 carbon atoms, a phenyl group, a phenoxy group, a cyano group and a nitro group). Specific examples of compounds of formula (2) include, for example, formula (31):

[Formula 9]

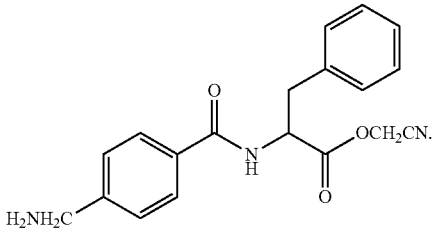  (31)

In yet another method, which is the third aspect for synthesizing a cyclic peptide compound, both Functional Group 1 and Functional Group 2 exist on amino acid residues that are incorporated in the peptide chain elongation reaction. An amino acid containing Functional Group 1 is a special (non-standard) amino acid, and it is incorporated in the peptide chain elongation reaction using the genetic reprogramming technology. Since the amino acid containing Functional Group 2 is a proteinogenic amino acid, and Functional Group 2 is basically a nucleophilic functional group (—SH, —COOH and —OH, etc.) contained in cysteine, tyrosine and the like, similar to the first aspect, Functional Group 1 should preferably be a functional group containing an appropriate leaving group, for example, a group of —CH$_2$-L (wherein, L is a leaving group, such as —Cl, —Br and —OSO$_2$CH$_3$).

Specific examples of amino acid compounds containing Functional Group 1 include a compound of formula (4):

[Formula 10]

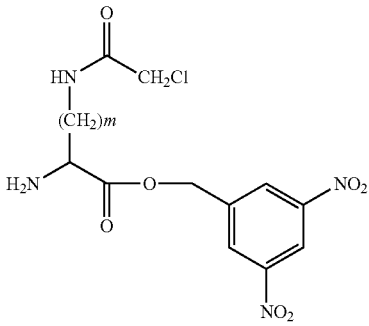  (4)

(wherein, m is an integer of 1 to 10). Specific examples of compounds of formula (4) include a compound whose m is 2. Such compound can be produced from 2,4-diamino butyric acid, for example. Cysteine is preferable as an amino acid compound containing Functional Group 2.

In yet another method, which is the fourth aspect for synthesizing a cyclic peptide compound, both Functional Group 1 and Functional Group 2 exist on amino acid residues that are incorporated in the peptide chain elongation reaction. An amino acid containing Functional Group 1 and an amino acid containing Functional Group 2 are both special (non-standard) amino acids, and they are incorporated in the peptide chain elongation reaction using the genetic reprogramming technology.

Functional Group 1 and Functional Group 2 may exist on the substituent on the nitrogen atom of the amino group, or on the substituent on the carbon atom, such as α-carbon and β-carbon. Functional Group 1 and Functional Group 2 should preferably exist on the substituent on the carbon atom, such as α-carbon and β-carbon. Groups mentioned in the second aspect can be given as examples of Functional Group 1 and Functional Group 2.

Specific examples of amino acids containing Functional Group 1 include compounds of formula (5) or formula (7):

[Formula 11]

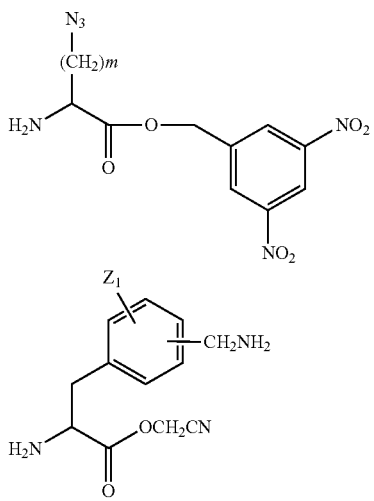

(wherein, $Z_1$ and m are the same as above). Specific examples of compounds of formula (7) include, for example, formula (32):

[Formula 12]

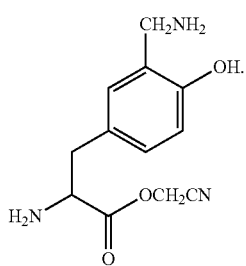

Specific examples of amino acids containing Functional Group 2 include compounds of formula (6) or formula (8):

[Formula 13]

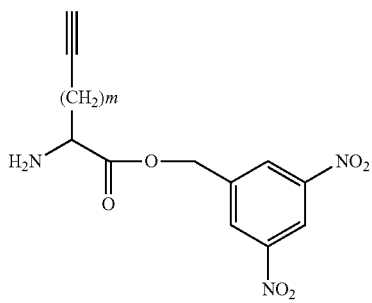

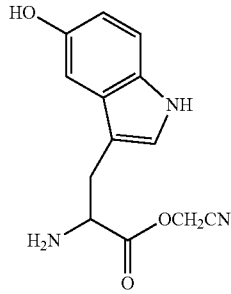

(wherein, m is the same as above).

Further, examples of combinations include a combination of a compound containing a functional group of (A-1) (e.g. a compound of formula (4) above), as an amino acid compound containing Functional Group 1, and a special (non-standard) amino acid containing a —SH group, such as homocysteine or mercapto norvaline, as an amino acid compound containing Functional Group 2.

A cyclic peptide compound can be synthesized by cyclizing a synthesized non-cyclilc peptide compound shown above. Conditions for the bonding reaction of Functional Group 1 and Functional Group 2 are determined according to the type of functional group pairs.

A non-cyclic peptide compound can be cyclized by putting the isolated non-cyclic peptide compound under appropriate reaction conditions. Or else, such compound can be cyclized without isolating the non-cyclic peptide compound by adjusting the in vitro translation system to an appropriate reaction condition. Depending on the type of the pair of functional groups, cyclization can be carried out under a condition of the in vitro translation system for synthesizing a non-cyclic peptide compound, in which case, the cyclic peptide compound can be obtained without particularly adjusting the reaction condition.

Cyclization of the non-cyclic peptide compound can be performed under the following reaction condition. For example, when the pair of functional groups is a pair of —CH$_2$-L (wherein, L is a leaving group, such as —Cl, and —Br) and a nucleophilic functional group —SH, the cyclization can be performed by heating the isolated non-cyclic peptide compound in the solvent (e.g. 40 to 100° C.), or by maintaining the in vitro translation system at 35 to 40° C. for a few hours (e.g. at 37° C. for 3 hours).

When the pair of functional groups is the pair (A) above, cyclization can be performed by heating the isolated non-cyclic peptide compound in an appropriate solvent (e.g. 40 to 100° C.), or by maintaining the in vitro translation system at 35 to 40° C. for a few hours (e.g. at 37° C. for 3 hours). Also, when the pair of functional groups is the pair (A) above, the reactivity of Functional Groups (A-1) and (A-2) are relatively high, so the reaction of the functional groups progresses in the in vitro translation system for synthesizing a non-cyclilc peptide compound and a cyclic peptide compound may be isolated by the in vitro translation system.

When the pair of functional groups is the pair (B) above, cyclization (Huisgen cyclization) can be performed to form (B-3) by treating the non-cyclic peptide compound, isolated by the in vitro translation system, with cuprous salt (prepared by reducing copper (II) sulfate by ascorbate in the system) in an appropriate solvent.

When the pair of functional groups is the pair (C) above, the isolated non-cyclic peptide compound can be treated with potassium ferricyanide (K3[FE(CN)$_6$]) in an appropriate solvent to induce reaction and form (C-3).

In the Examples below, a cyclic peptide obtained by a translation-synthesis of a peptide sequence having a chloroacetyl group and cysteine each positioned on one of the two ends thereof is provided as an example of a substance that can be cyclized under conditions of the in vitro translation system. In such example, a peptide containing a chloroacetyl group as Functional Group 1 is synthesized using the genetic code reprogramming technology. When a cysteine residue is positioned in the peptide, the thiol group voluntarily attacks the chloroacetyl group nucleophilically after translation, and the peptide cyclizes by a thioether bond. To incorporate a chloroacetyl group in the N terminal of peptide, the peptide is synthetized by adding an initiator tRNA acylated by an amino acid having a chloroacetyl group to the translation system. Or else, the chloroacetyl group can be situated in an area other than the N terminal, in which case an elongator tRNA acylated by an amino acid containing a chloroacetyl group is used.

In Vitro Translation System

A translation system is a concept that includes both a method for the translation-synthesis of peptide and a kit (product) thereof. The in vitro translation system to be used in the present invention for preparing the non-standard peptide library should preferably be constructed as a system with less impurity by dividing the known reconstituted translation system. The specific components of the translation system as a kit (product) usable in the present invention are explained below by comparison with conventional systems.

Specific examples of the components of the translation system include a ribosome, IFs, EFs, RFs, RRF, a set of natural amino acid/tRNA/specific ARS protein enzyme minimally required for synthesizing the desired peptide.

The ribosome to be used is preferably isolated from *E. coli* and refined.

The protein facters to be used are translation initiation factors (e.g. IF1, IF2, IF3), translation elongation factors (e.g. EF-Tu, EF-Ts, EF-G), translation release factors (e.g. RF1, RF2, RF3, RRF) and enzymes for regenerating energy sources (e.g. creatine kinase, myokinase, pyrophosphatase, nucleotide-diphosphatase kinase). Of these, the translation release factors and enzymes for regenerating energy sources are added by option. T7 RNA polymerase may be added for the transcription from the template DNA, but RNA polymerase does not need to be added when an mRNA that has been transcribed in advance is added.

In addition, an appropriate buffer, NTPs as an energy source of translation reaction, a Creatine phosphate, factors required for activating ribosome, stabilizing RNA and stabilizing protein may be used as necessary. Further, a formyl donor like 10-formyl-5,6,7,8-tetrahydroforlic acid (Baggott et al., 1995) is essential in a conventional translation reaction, since N-formylmethionine is specified for the initiator codon AUG by the initiator tRNA, but such formyl donor is optional when initiating the translation reaction by a special (non-standard) amino acid in the present invention. Likewise, methionyl-tRNA formyltransferase (MTF) is not always necessary.

The translation system used in the present invention can use a natural tRNA and ARS, corresponding to the natural proteinogenic amino acid, as in conventional systems. Examples of natural tRNAs are mixtures of purified tRNA fractions obtained from collecting and crushing *E. coli*, which can also be obtained on the market. Some A, U, C and G in the natural tRNA are chemically modified by enzymes. Alternatively, tRNA having a naturally occurring sequence, albeit transcribed in the test tube, can also be used. In contrast, an artificial tRNA that is a transcription product of tRNA is preferably used as an orthogonal tRNA instead of natural tRNA. An artificial tRNA can be prepared by an in vitro transcription reaction using a template. DNA and an appropriate RNA polymerase. Such artificial tRNAs do not include any chemical modification. When the translation product is a non-standard peptide with no proteinogenic amino acid included therein, the synthesis of the non-standard peptide can be performed using only artificial tRNAs, and natural tRNA for proteinogenic amino acids and ARS are not required.

To incorporate one or more special (non-standard) amino acids into the peptide that is the translation product, orthogonal initiator or elongator tRNA each acylated by a special (non-standard) amino acid are added to the translation system in advance. In preferable embodiments, a tRNA acylated by a special (non-standard) amino acid is prepared by binding a special (non-standard) amino acid to the 3' terminal of the isolated orthogonal tRNA using flexizyme under a condition in which no other tRNA or ARS exists. A tRNA charged chemically or enzymatically with a special (non-standard) amino acid can also be used, in principle.

Template Nucleic Acid Encoding a Non-Standard Peptide

In the present invention, a library of peptides with random amino acid sequences is synthesized using an in vitro translation system that conducts a translation-synthesis from template nucleic acids (mRNAs or corresponding DNAs) having a random sequence in the region coding for a peptide. Further, the translation system is combined with an in vitro display technology so that the screening is conducted with peptides constituting the library being accompanied by the encoding nucleic acid sequences. In other words, peptide aptamers are selected from a display library in which genetic information is displayed in the form of a peptide, which is the translation product. Accordingly, each random peptide molecule in the library is tagged with a tag that can be amplified and read, through a method of molecular biology.

An in vitro display is a display of peptides paired with genetic information, the peptides synthesized using a cell-free translation system (also known as an in vitro translation system), and in vitro displays known in the art include a ribosome display, an mRNA display, a DNA display, a RAPID display, PD display and the like. All given displays include a mechanism of conjugating a genetic information recorded in the mRNA or the DNA and a peptide coded for by the genetic information to pair them together as a [genetic information]-[translation product] complex. Three components, namely mRNA-ribosome-peptide, form a complex in the ribosome display. An mRNA-peptide complex is formed in the mRNA display, RAPID display, and PD display. A DNA-peptide complex is formed in the DNA display. Any in vitro display library can be used in the present invention.

The present invention is designed so that the sequences of template RNAs or DNAs corresponding to the amino acid sequences of the peptide encode a random library of non-standard peptides. Specifically, the base sequence comprises a region encoding a peptide, the region including a random sequence of a repetition of multiple triplets that differ with each other and at least a part of the triplets in the random sequence corresponding to one or more artificial codons that each specifies a special (non-standard) amino acid.

In another aspect of the present invention, the RNA or DNA sequence is designed to encode a cyclic non-standard peptide. Specifically, the region encoding a peptide in the base sequence comprises base sequences corresponding to (a) to (c) below, in that order, along the mRNA sequence from 5' to 3':

(a) a codon specifying an amino acid containing Functional Group 1;
(b) a random sequence consisting of repetitions of multiple different triplets; and
(c) a codon specifying an amino acid containing Functional Group 2.

A random mRNA sequence is designed so that special (non-standard) amino acids appear with a certain probability in the random amino acid sequence obtained by translation. That is, since at least some of the triplets in the random sequence of (b) are artificial codons specifying special (non-standard) amino acids, one or more special (non-standard) amino acids are incorporated into the amino acid sequence of the random peptide as the translation product. The incorporation of a special (non-standard) amino acid is achieved by the pairing of an anticodon of the tRNA for elongation reaction, carrying the special (non-standard) amino acid, and an artificial codon specifying the special (non-standard) amino acid in the peptide chain elongation reaction on the ribosome. Further, the peptide, which is a translation product, is cyclized by the bond forming reaction between Functional Group 1 and Functional Group 2, a pair of functional groups capable of forming a bond. As mentioned above, the tRNA used in the introduction of a special (non-standard) amino acid is preferably an artificial tRNA prepared by an in vitro transcription reaction.

In the present invention, DNA or RNA molecules corresponding to base sequences that constitute translation templates are added for use with an in vitro translation system consisting of ingredients optimized for its purpose. Base sequences that are advantageous for translation can be additionally included in the nucleic acid sequence in addition to the region that encodes the desired amino acid sequence, according to the translation system to be used, similar to a protein expression system using living cells. An example is a system using an *E. coli* derived ribosome, which shows that the translation reaction becomes more efficient when a Shine-Dalgarno (SD) sequence or an epsilon sequence is included upstream of the initiator codon.

An initiator codon is placed at the N terminal of the peptide-encoding region. The initiator codon is normally a triplet sequence AUG. However, in the present invention, other base sequences can be used as the initiator codon, in addition to the AUG codon, since the anticodon sequence of the initiator tRNA synthesized by an in vitro transcription reaction can be set to any sequence, enabling the reprogramming of the initiator codon.

In the C terminal side is included a sequence to conjugate the nucleic acid molecule and its translation product, namely a peptide, to form an in vitro display. For example, when using an mRNA display method that uses a puromycin linker, an mRNA library of mRNAs each previously conjugated with a puromycin linker can be added to the translation system to form an mRNA-peptide complex library. A linker is normally inserted between the 3' terminal of mRNA and puromycin to enable efficient introduction of puromycin onto the A site of ribosome. Puromycin functions as a substrate (aminoacyl tRNA analog) for the transpeptidation reaction on the ribosome, and binds to the C terminal of the nascent peptide to conjugate mRNA and peptide. The mRNA display method is a technology for integrating a genotype with a phenotype by conjugating mRNA and peptide via an appropriate linker in an in vitro translation system. It is within the understanding of a person skilled in the art that a linker containing a substance with a function similar to puromycin can replace puromycin, as long as the above object is achieved.

Another method that can be used is a method of forming an mRNA-peptide complex library by hybridization of a linker and an mRNA in the in vitro translation system, instead of using an mRNA that has been previously conjugated with a linker. For example, an mRNA-peptide complex library is formed by inducing phenylalanine linkers (3'-phenylalanine-ACCA-PEG-[a base sequence complementary with the 3' terminal regions of an mRNA library]-5') prepared using a flexizyme to form complementary chains with the mRNA library (The "RAPID display method" disclosed in the unpublished Japanese patent application No. 2009-243240). In such case, the base sequence for hybridizing with the linker will be included downstream of a region in mRNA that encodes a peptide (3' terminal region).

In the specific Examples below, the initiator codon AUG is placed at the N terminal of a peptide, and the codon UGC encoding cysteine (Cys), which is an amino acid containing Functional Group 2, is placed at the C terminal of the same peptide, with a codon encoding GlySerGlySerGlySer, which is a linker, placed immediately thereafter, and the sequence between AUG and UGC forming a random sequence.

A random sequence is composed of a repetition of condons consisting of triplets of any given sequences, which is designed such that some of the condons are artificial codons that each specifies a special (non-standard) amino acid such as N-methyl amino acid.

A possible sequence is described by representing a triplet constituting the random sequence with a $N^1N^2N^3$ codon. $N^1$ and $N^2$ can be independently one of A, U, C or G. $N^3$ can also be one of A, U, C or G. Or else, $N^3$ can be one of any three types of bases selected from the four bases, A, U, C and G. Or else, $N^3$ can be one of any two types of bases selected from the four bases, A, U, C and G. Or else, $N^3$ can be determined to be one of A, U, C or G.

Examples of triplets on the mRNA sequence constituting a random sequence include an NNU codon or an NNK codon {wherein, N is a ribonucleotide that is one of A, U, C or G, and K is a ribonucleotide that is one of C or G}.

Explained below according to the Examples, without being limited thereby, is an exemplary peptide sequence that is obtainable by a random mRNA library containing mRNAs whose codons are NNU (wherein, N is one of A, U, C or G codon), comprises $N^\alpha$-chloroacetyl-D-tryptophan and cysteine for cyclization reaction, and to which 4 types of N-methyl amino acids are incorporated.

For example, the number of types of codons generated from an NNU triplet is 16 (4×4×1=16), and to 4 codons were assigned 4 types of N-methyl amino acids (N-methylglycine [AUU], N-methylalanine [GCU], N-methylserine [CUU], N-methylphenylalanine [UUU]). To the remaining 12 codons were assigned 11 types of proteinogenic amino acids (serine [UCU and AGU], tyrosine [UAU], cysteine [UGU], proline [CCU], histidine [CAU], arginine [CGU], threonine [ACU], asparagine [AAU], valine [GUU], aspartic acid [GAU], glycine [GGU]). The open reading frame on the mRNA encoding a cyclic N-methyl peptide was 5'-AUG(NNU)$_{8-15}$UGC-3'. $N^\alpha$-chloroacetyl-D-tryptophan was assigned to AUG and cysteine was assigned to UGC, and the codon table was designed to form a cyclic peptide without fail. The Example of the above included the NNU codon repeated 8 to 15 times to prepare cyclic peptides of various sizes.

TABLE 2

| First base of the codon | Second base of the codon | | | | Third base of the codon |
|---|---|---|---|---|---|
| | U | C | A | G | |
| U | $^{Me}$Phe | Ser | Tyr | Cys | U |
| | | | | | C |
| | | | | | A |
| | | | | | G |
| C | $^{Me}$Ser | Pro | His | Arg | U |
| | | | | | C |
| | | | | | A |
| | | | | | G |
| A | $^{Me}$Gly | Thr | Asn | Ser | U |
| | D-$^{ClAc}$Trp | | | | C |
| | | | | | A |
| | | | | | G |
| G | Val | $^{Me}$Ala | Asp | Gly | U |
| | | | | | C |
| | | | | | A |
| | | | | | G |

The advantage of the NNU library is the ability to construct a library of high accuracy, since no stop codons specified by UAA, UAG and UGA appear in the random region. Further, the introduction rate of N-methyl amino acid in peptide can be theoretically raised to 25%, since 4 out of 16 codons each specify an N-methyl amino acid. An NNU library was used in the present case, but an NNK (wherein, K is C or G) library and other libraries of combinations including different bases at the $3^{rd}$ position may be used, and 32 codons (4×4×2=32) may be used. When 4 types of N-methyl amino acids are incorporated in such cases, the rate of N-methyl amino acid appearing decreases by half.

The codon on mRNA is paired with an anticodon on a corresponding tRNA. Possible pairs include not just Watson-Crick base pairs but also other combinations, since a wobble base pair is accepted for the $3^{rd}$ letter in the codon and the $1^{st}$ letter in the anticodon. For example, the third base U in the NNU codon can be paired with G or A, the third base C on the NNK codon can be paired with G, and the third base G on the NNK codon can be paired with U or C. A GNN anticodon is an example of a preferable anticodon to be combined when using an NNU codon to incorporate an N-methyl amino acid in the present invention.

Aminoacylation by Flexizymes

The flexizyme is an RNA catalyst (ARS ribozyme) that functions to acylate an amino acid substrate with a desired structure to any given tRNA. The flexizyme differs from a natural ARS protein enzyme; it does not exhibit specificity to any amino acid or tRNA, and it can perform aminoacylation with any amino acid that does not inherently charge a given tRNA. A special (non-standard) amino acid is incorporated in the peptide sequence in the present invention by adding an orthogonal tRNA that has been acylated with a special (non-standard) amino acid using flexizymes to the in vitro translation system.

The orthogonal tRNA is a tRNA that is not aminoacylated in the translation system since it is not recognized by a naturally derived ARS (e.g. an ARS protein enzyme derived from E. coli) inherent in the translation system, but that can efficiently express the amino acid specified as a pair to the mRNA codon in the peptide synthesis reaction on the ribosome. Examples of orthogonal tRNAs to be used include a natural suppressor tRNA derived from different species, or an artificially constructed tRNA. As mentioned above, a single species of orthogonal tRNA that is an artificial transcription product is preferably used in the present invention for introduction of special (non-standard) amino acids.

The flexizyme has a catalytic ability to perform acylation on adenosine on the 3' terminal using an activated amino acid ester as the substrate, and recognizing the carbonyl group which is a reaction point of the amino acid, the aromatic ring which is an amino acid side chain or a leaving group, and the 5'-RCC-3' sequence section (R=A or G) on the 3' terminal of tRNA. The flexizyme has no specificity to the anticodon section of tRNA. That is, the anticodon section of tRNA may be modified to any sequence without affecting the efficiency of aminoacylation. The flexizyme links any given special (non-standard) amino acid with any given codon by conjugating an optional special (non-standard) amino acid to a tRNA having an optional anticodon sequence. Therefore, a library with any given special (non-standard) amino acid incorporated therein can be prepared.

Flexizyme structures (RNA sequence) known in the art are shown below. The original flexizyme Fx

SEQ ID NO: 1
[GGAUCGAAAGAUUUCCGCAGGCCCGAAAGGGUAUUGGCGUUAGG

U-3', 45nt]

Dinitrobenzyl flexizyme dFx

SEQ ID NO: 2
[5'-GGAUCGAAAGAUUUCCGCAUCCCCGAAAGGGUACAUGGCGUUAGG

U-3', 46nt]

Enhanced flexizyme eFx

SEQ ID NO: 3
[5'-GGAUCGAAAGAUUUCCGCGGCCCCGAAAGGGGAUUAGCGUUAGG

U-3', 45nt])

Aminoflexizyme aFx

SEQ ID NO: 4
[5'-GGAUCGAAAGAUUUCCGCACCCCCGAAAGGGGUAAGUGGCGUUAG

GU-3', 47nt])

Unlike the natural ARS protein enzyme, the flexizyme functions as a catalyst only in the process for binding the amino acid substrate to tRNA, skipping the first step of aminoacylation, which is a process of generating a high energy intermediate (aminoacyl AMP). Accordingly, the amino acid substrate used therewith needs to be an amino acid activated in advance at a low level. That is, the adenylation of the amino acid, which has been skipped, is replaced by the use of an amino acid derivative having an ester bond activated at a low level at the carbonyl group where acylation proceeds. Normally, activation of the acyl group can be achieved by an ester bond of an electron-withdrawing leaving group, but an ester having an electron-withdrawing leaving group that is too strong, causes hydrolysis and simultaneously induces acylation of a random RNA. Hence, the amino acid substrate to be used should be that activated at a low level to prevent such secondary reaction in the absence of a catalyst. Such low-level activation can be implemented using AMP, cyanomethylester, thioester or benzyl esters possessing an electron-withdrawing functional group, such as a nitro group or a fluorine group. Examples of preferably amino acid substrates include aminoacyl-cyanomethyl ester (CME: cyanomethyl ester), aminoacyl-dinitrobenzyl ester (DNB: 3,5-dinitrobenzyl ester), or an aminoacyl-4-chlorobenzyl thioester (CBT: p-chloro-benzyl thioester), without being limited thereby.

Further, the amino acid substrate must contain an aromatic ring in the amino acid side chain or the leaving group to be recognized by the flexizyme. In the present specification, an amino acid substrate having an appropriate leaving group as a substrate of a flexizyme is also referred to as an activated amino acid ester. For example, concerning N-methylphenylalanine, the use of N-methylphenylalanine CME as a substrate causes the formulation of a tRNA charged with N-methylphenylalanine by mixing eFx and tRNA. The substrate of eFx can be an activated amino acid of an amino acid having an aromatic group on its side chain, and no aromatic group is required as an active group. Also, concerning N-methylglycine, N-methylalanine, N-methylserine, the respective DNB derivatives can be used as the substrate to be mixed with dFx and tRNA to formulate a tRNA charged with N-methyl amino acid. The dFx is not limited to the side chain of the amino acid, since it recognizes an aromatic group as an active group.

Acylation mediated by the flexizyme can be carried out in a solution, or by using a column that uses an ARS ribozyme fixed to the carrier. For example, if the reaction scale of translation is low, namely 100 μL or lower, then tRNA can be acylated in the solution using flexizyme, the reaction solution can be precipitated with ethanol to produce a pellet to be dissolved in an appropriate buffer (e.g. 1 mM of potassium acetate, pH5 etc.), and the product can be added to the translation system. A desirable condition can be appropriately selected as the reaction condition, and an example of the reaction condition for a small scale is as follows: pH 7.5, 0.1 M of reaction buffer comprising 0.5 to 20 μM of tRNA, 0.5 to 20 μM of flexizyme, 2 to 10 mM of amino acid substrate and 0.6 M of $MgCl_2$ by the final concentration can be subjected to reaction at 0° C. for 1 to 24 hours.

When the reaction scale of translation is beyond 100 μL, it is more preferable to use a flexizyme fixed to the carrier in view of recycling the flexizyme. Carriers to be used include, without limitation, resin, agarose, sepharose, and magnetic beads. The reaction can be performed, for example, by the method taught in Murakami, H., Bonzagni, N.J. and Suga, H. (2002). "Aminoacyl-tRNA synthesis by a resin-immobilized ribozyme." J. Am. Chem. Soc. 124(24): 6834-6835 when fixing the flexizyme to the carrier. The reaction product, namely the aminoacylated tRNA, can be separated by various methods. An example is to elute it from the column using a buffer containing about 10 mM of EDTA. A resin having an ARS ribozyme fixed thereto can be recycled more than 10 times after it is equilibrated with a reaction buffer.

Explained in the Examples below is an example of incorporating to the amino acid sequence 4 types of N-methyl amino acids (N-methylglycine, N-methylalanine, N-methylserine, N-methylphenylalanine) conjugated with tRNA$^{Asn}$-E2 using flexizymes according to the teaching of Kawakami et al. (Non-patent Document 11). A tRNA$^{Asn-E2}_{NNN}$ is an artificial tRNA produced by modifying tRNA$^{Asn}$, which is a tRNA for elongation reaction derived from E. coli, and the anticodon sequence (NNN, wherein N is an optional base) can be modified in various ways for use. The artificial tRNA is orthogonal to natural ARS, so it will not be charged by a natural amino acid in the translation system, but it is accepted without any problem in the peptide chain elongation reaction on the ribosome. That is, the aminoacyl tRNA, which is a conjugation of the artificial tRNA and the special (non-standard) amino acid, will bind to the elongation factor (EF-Tu), then it will be carried to site A on the ribosome to be used in the peptide chain elongation process. The tRNA$^{Asn-E2}$ is an example of an elongator tRNA for acylating a special (non-standard) amino acid, and it is actually confirmed as usable in the specific in vitro translation system used in the Examples. However, the tRNA for elongation usable in the present invention is not limited thereby. A person skilled in the art will understand that the tRNA that can be used to incorporate special (non-standard) amino acids in the peptide chain elongation reaction of the present invention can be selected as necessary according to the in vitro translation system to be used.

Further, if the amino acid having a functional group for cyclization in the present invention is a special (non-standard) amino acid, the special (non-standard) amino acid will still be bound to an orthogonal tRNA having an optional anticodon by use of a flexizyme. In an embodiment of the present invention, an amino acid having Functional Group 1 is placed as an initiator amino acid residue. In such a case, the initiator tRNA can be charged with an amino acid having a functional group for cyclization to incorporate a functional group for cyclization into the N terminal of the peptide.

In the Examples below, N$^\alpha$-chloroacetyl-D-tryptophan, which is a tryptophan of the D configuration having a chloroacetyl group, was conjugated to tRNA$^{fMet}$ which is an initiator tRNA to be incorporated into the N terminal of peptide. The chloroacetyl group incorporated into the peptide starts a voluntary $S_N2$ reaction with the thiol group of the cysteine residue in the peptide, cyclizes peptide by a thioether reaction (Goto et al., ACS Chem. Biol., 2008, 3, 120-129). A D-tryptophan is used as the mother nuclei in this example, but a peptide library can be created without any problem using the L-tryptophan as well as the D configuration of the other 19 types of proteinogenic amino acids.

Note that the translation-synthesis of a model cyclic N-methyl peptide having a specific sequence that incorporates 4 N-methyl amino acids and a phenylalanine having a chloroacetyl group is achieved by Kawakami et al. (Non-patent Document 11). However, the present application is the first to disclose the construction of a library.

Initiator tRNA and Elongator tRNA

The fact that an initiator tRNA is used only to initiate translation and not in the elongation reaction, whereas the elongator tRNA is not used in the initiation reaction, is important. The same differentiation of the initiator tRNA and the elongator tRNA exists in the present invention.

An artificial tRNA is preferably used to acylate special (non-standard) amino acids in the present application. An example, without limitation, of an artificial tRNA that is an elongator tRNA is the tRNA$^{Asn-E2}$. The base sequence of the tRNA is based on the natural tRNA$^{Asn}$ of E. coli:

(SEQ ID NO: 9)
(5'-UCCUCUG$^{s4}$UAGUUCAGDCGGDAGAACGGCGGACUQUU$^{t6}$AAΨCCG

UAU$^{m7}$GUCACUGGTΨCGAGUCCAGUCAGAGGAGCCA-3')

($s^4$U: 4-thiouridine, D: dihydrouridine, Q: queuosine, $^{t6}$A: 6-threonylcarbamoyladenine, Ψ: pseudouridine, $^{m7}$G:7-methylguanosine, T: ribothymidine). The present inventors removed modification bases from and introduced mutation to the natural tRNA and created a tRNA$^{Asn-E2}$ that is a tRNA for elongation reaction that is not aminoacylated by the 20 types of aminoacylation enzymes of E. coli through in vitro transcription. The section shown by NNN represents an anticodon, which is modified in accordance with the codon. (tRNA$^{Asn-E2}$:

5'-GGCUCUGUAGUUCAGUCGGUAGAACG-GCGGACU<u>NNN</u>AAUCCGUAUGUCACUG GUUC-GAGUCCAGUCAGAGCCGCCA-3' (SEQ ID NO: 5) [Sections where modification was removed, total 8 sections. $^{s4}$U8U, D16U, D20U, $^{t6}$A37A, Ψ39U, $^{m7}$G46G, T54U, Ψ55U. The 34$^{th}$ Q is an anticodon, so it is modified in accordance with the codon] [Mutated sections, total 4 sections. U1G, C2G, G71C, G72C])

An example, without limitation, of an artificial tRNA that is an initiator tRNA is the tRNA$^{fMetE}$. The base sequence of the tRNA is based on the natural tRNA$^{fMetE}$ of E. coli:

(SEQ ID NO: 10)
(5'-CGCGGGG$^{s4}$UGGAGCAGCCUGGDAGCUCGUCGGGCmU<u>CAU</u>AACCC

GAAGAUCGUCGGTΨCAAAUCCGGCCCCCGCAACCA-3')

(Cm: 2'-O-methylcytidine). The present inventors created a tRNA$^{fMetE}$ that is a tRNA for initiation reaction, which differs from the natural tRNA in that its modification base is removed and its first base in the 5' terminal, C, is changed to G, through in vitro transcription. The CAU section represents the anticodon corresponding to the AUG initiator codon. (tRNA$^{fMetE}$ used in the present invention: 5'-GGCGGGGUGGAG CAGCCUGGUAGCUCGUCGGGCU CAUAACCCGAAGAUCGUCGGUUCAAAUCCGG CCCCCGCAACCA-3' (SEQ ID NO: 6) [Sections where modification was removed, total 6 sections. $^{s4}$U8U, D20U, Cm32C, T54U, Ψ55U.] [Mutated sections, total 1 section. C1G]) An important point for an initiator tRNA is that the first base (C in a natural tRNA$^{fMet}$ and G in the tRNA$^{fMet}$ of the present application) of the 5' terminal does not form a complementary chain with the 72$^{nd}$ base (A in both a natural tRNA$^{fMet}$ and the tRNA$^{fMet}$ of the present application). This non-complementary chain transfers a formyl group to the Met-tRNA$^{fMet}$ by the methionyl formyl transferase (MTF) (however, it is meaningless if an initiator special (non-standard) amino acid such as chloroacetyl tryptophan is used in this section) and regulates the EF-Tu bond.

In Vitro Selection

The non-standard peptide library constructed in the present invention by the in vitro translation system is completely compatible with in vitro display technologies, such as the mRNA display, so that a peptide molecule that binds with the target can be created from non-standard peptide libraries of a large variety of 10$^{13}$ types or more.

The in vitro display technology is used as a tool in molecular evolution engineering. In molecular evolution engineering, numbers of genes are prepared as possible candidates for formulating proteins and peptides with desired functions and features, from which a clone having the targeted phenotype is selected. The basic procedure is to first prepare a DNA population (DNA library), obtain an RNA population (RNA library) as the in vitro transcription product, and also obtain a peptide population (peptide library) as the in vitro translation product. From the peptide library, a peptide with the desired function or feature is selected by a suitable screening system. For example, to obtain a peptide molecule that binds to a specific protein, a peptide group can be poured into a column containing a solid-phased target protein to recover a mixture of peptide molecules bound to the column. The recovered peptides are tagged with nucleic acid molecules, which were their templates, by the in vitro display technology. In an mRNA display library, the peptide molecules are each tagged with an mRNA. Accordingly, a similar selection experiment is performed again after the recovered group of peptide-mRNA complex is converted back to DNA by reverse transcriptase and amplified by PCR to obtain a biased library containing numbers of clones having a desired phenotype. Or else, the reverse transcription can be performed before selection to form the nucleic section into a double chain (DNA/RNA hybrid) and thus avoid the risk of recovering RNA aptamers. A repetition of such process enriches clones with a desired phenotype in the group as generation progresses.

When identifying peptide aptamers, a gene of a peptide aptamer to bind to the target substance can be cloned by repeating the process of mixing an in vitro display library with the target substance, selecting the pairing molecule (active species) to indicate the peptide bound to the target substance, and preparing the nucleic acid library from the nucleic acid section of the selected pairing molecule using PCR.

Generally speaking, the target substance includes protein, nucleic acid, sugar, fat and any other compound.

To select active species, it is necessary to bring the [genetic information]-[peptide] complex in contact with the target substance and to separate the complex that indicates the peptide bound to the target substance from the many other complexes that are not bound to the target substance by a suitable method for their recovery. Many technologies are known in the art as methods of recovery.

One exemplary, useful method is to modify the target substance so that it can be recovered through binding with the solid phase. For example, in the Example below, the target substance is modified beforehand by biotin to be recovered using specific binding with a solid-phased protein bound to biotin. Examples of specific binding that can be used include a combination of protein bound to maltose/maltose, polyhistidine peptide/metal ion (nickel, cobalt, etc.), glutathione-S-transferase/glutathione, antibody/antigen (epitope) in addition to a combination of protein bound to biotin/biotin (avidin, streptavidin, etc.), without limitation.

The present invention includes formulating non-standard peptides binding to the target substance through repeating in vitro selection, comprising bringing the peptide library in contact with the target substance, selecting an active specie that displays peptide binding to the target substance, amplifying the nucleic acid sequence of the selected active specie, and selecting the active specie from the peptide library that has been re-synthesized by the in vitro translation system using the amplified nucleic acid sequence as the template.

Formulating non-standard peptides binding to the target substance includes recovering the active species that indicate peptides bound to the target substance to analyze the nucleic acid sequence, determining the peptide sequence from the nucleic acid sequence, and selecting an appropriate non-standard peptide based on the obtained peptide sequence to obtain the amino acid sequence of the non-standard peptide binding to the target substance and the nucleic acid sequence. Further, the obtained sequence information can be used as a basis for synthesizing, refining and isolating a non-standard peptide using any given method. A non-standard peptide with high activity can be obtained by using the obtained peptide and assessing their binding with the target protein as well as their inhibition activity of the target protein.

In the Example below, the ubiquitin ligase E6AP was focused on as the target substance, and a cyclic N-methyl peptide that specifically binds to the C terminal domain of E6AP known as E6AP-HECT was obtained.

In addition to the above description, the materials and methods for performing the present invention follow the conventional methods well known in the technological fields of chemistry and molecular biology, and methods described in various general text books and specialized reference documents are used, unless otherwise specified.

The present invention is specifically described by Examples below. These Examples are intended to describe the present invention without limiting the scope of the present invention.

EXAMPLE

Example 1

Creating the NNU mRNA Library (FIG. 1)

The mRNA library for constructing the cyclic N-methyl peptide library was prepared as follows.

Eight DNA primers having random regions in which 8 to 15 units of NNA (N=A or T or C or G) are arranged consecutively, were purchased from Operon Biotechnologies.

```
(NNUpool 8. R69
                                        SEQ ID NO: 11
[5'-GCTGCCGCTGCCGCTGCCGCAANNANNANNANNANNANNANNANN

CATATGTATATCTCCTTCTTAAAG-3'],

NNUpool 9. R7
                                        SEQ ID NO: 12
[5'-GCTGCCGCTGCCGCTGCCGCAANNANNANNANNANNANNANN

ANNCATATGTATATCTCCTTCTTAAAG-3'],

NNUpool 10. R75
                                        SEQ ID NO: 13
[5'-GCTGCCGCTGCCGCTGCCGCAANNANNANNANNANNANNANN

ANNANNCATATGTATATCTCCTTCTTAAAG-3'],

NNUpool 11. R78
                                        SEQ ID NO: 14
[5'-GCTGCCGCTGCCGCTGCCGCAANNANNANNANNANNANNANN

ANNANNANNCATATGTATATCTCCTTCTTAAAG-3'],

NNUpool 12. R81
                                        SEQ ID NO: 15
[5'-GCTGCCGCTGCCGCTGCCGCAANNANNANNANNANNANNANN

ANNANNANNANNCATATGTATATCTCCTTCTTAAAG-3'],

NNUpool 13. R84
                                        SEQ ID NO: 16
[5'-GCTGCCGCTGCCGCTGCCGCAANNANNANNANNANNANNANN

ANNANNANNANNANNCATATGTATATCTCCTTCTTAAAG-3'],

NNUpool 14. R87
                                        SEQ ID NO: 17
[5'-GCTGCCGCTGCCGCTGCCGCAANNANNANNANNANNANNANN

ANNANNANNANNANNANNCATATGTATATCTCCTTCTTAAAG-3'],

NNUpool 15. R90
                                        SEQ ID NO: 18
[5'-GCTGCCGCTGCCGCTGCCGCAANNANNANNANNANNANNANN ANNANNANNANNANNANNANNCATATGTATATCTCCTTCTTAAAG-3'])
and T7g10M.F48
                                         SEQ ID NO: 7
(5'-TAATACGACTCACTATAGGGTTAACTTTAAGAAGGAGATAT

ACATATG-3')

CGS3an13.R39
                                         SEQ ID NO: 8
5'-TTTCCGCCCCCCGTCCTAGCTGCCGCTGCCGCTGCCGCA-3').
```

Using T7g10M.F48 and each of the NNU pool primers, an elongation reaction was performed by Taq polymerase (94° C., 1 min→[50° C., 1 min→72° C., 1 min]×10 cycles→72° C., 5 min). Then, using the elongation product as the template, T7g10M.F48 and CGS3an13.R39 were used to perform PCR by Taq polymerase (94° C., 1 min→[94° C., 40 sec→61° C., 40 sec→72° C., 40 sec]×4 cycles→72° C., 5 min).

Then, using the PCR product, transcription was performed using T7RNA polymerase, and a separation-refinement was performed with an 8% polyacrylamide gel comprising 8M urea to obtain mRNAs at 20 µM each.

The mRNA is arranged in sequence from the 5' terminal side as follows:
G of the T7 promoter 3' terminal;
epsilon sequence (5'-UUAACUUUAA-3') SEQ ID NO: 19;
Shine-Dalgarno sequence (5'-AAGGAGA-3');
a translation region (5'-AUG[NNU]$_{8-15}$UGC-3');
a peptide linker region (5'-GGCAGCGGCAGCGGCAGC-3') SEQ ID NO: 20;
a complementary chain forming region of puromycin linker (5'-UAGGACGGGGGGCGGAAA-3') SEQ ID NO: 21.

The mRNAs having random sequences, from NNU8 to NNU15, were mixed at respective ratio of $1/16^3$, $1/16^2$, 1/16, 1, 1.4, 1.4, 1.4, 1.4 to form a 10 uM mRNA library.

Example 2

Figures 1, 2:
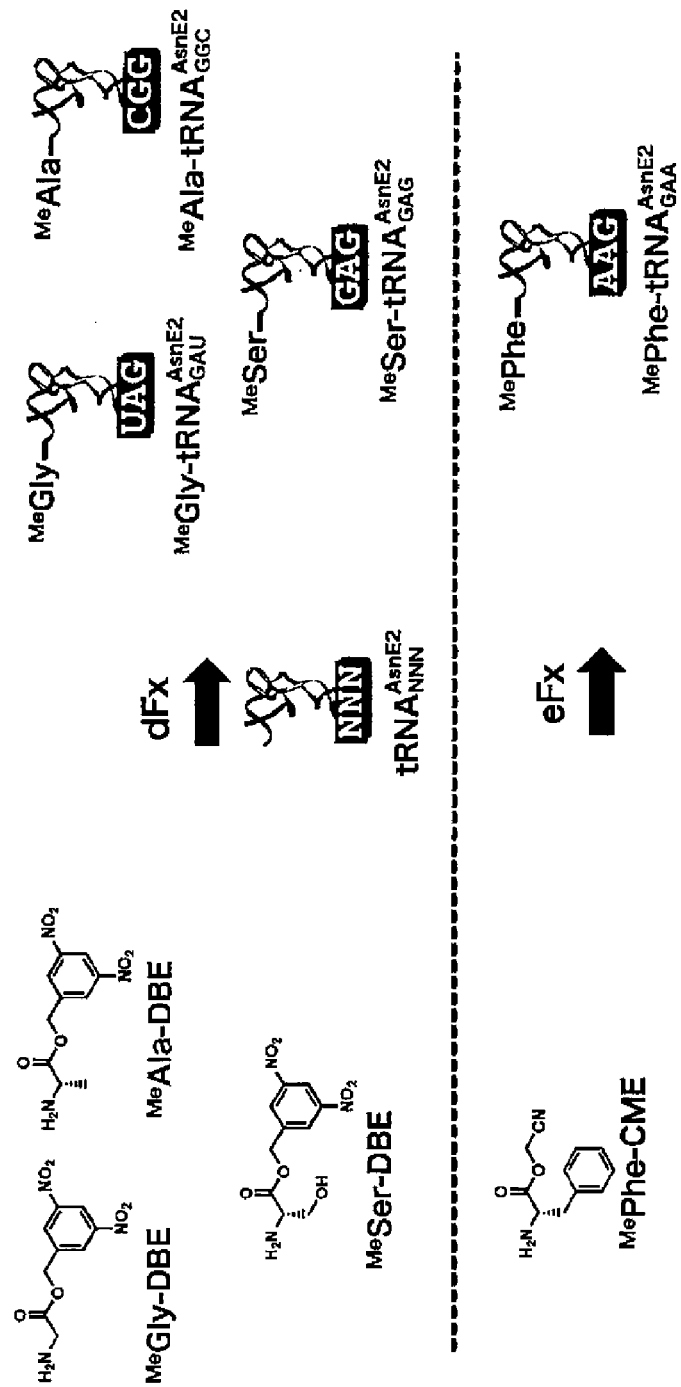
Figure 2:
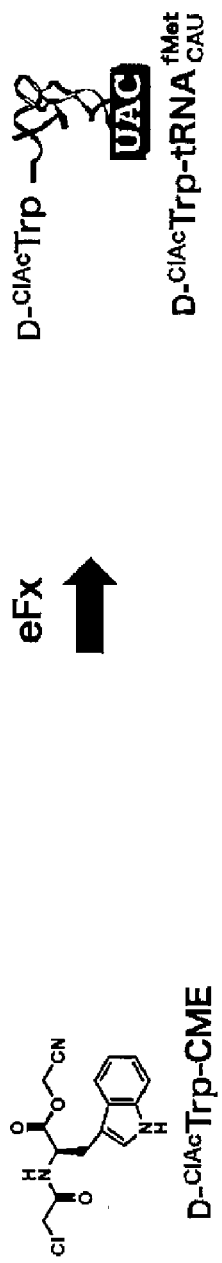

Preparation of Aminoacyl-tRNA (FIG. 2)

Four N-methyl amino acids were selected, namely N-methylglycine ($^{Me}$Gly), N-methylalanine ($^{Me}$Ala), N-methylserine ($^{Me}$Ser), N-methylphenylalanine ($^{Me}$Phe). Then, N-methylglycine dinitrobenzyl ester (MeGly-DBE), N-methylalanine dinitrobenzyl ester ($^{Me}$Ala-DBE), N-methylserine dinitrobenzyl ester ($^{Me}$Ser-DBE), N-methylphenylalanine cyanomethyl etser ($^{Me}$Phe-CME) were prepared as the activated ester derivatives of the above N-methyl amino acids, i.e., dinitrobenzyl ester (DBE) or cyanomethyl etser (CME).

Dinitrobenzyl flexizyme dFx was used as the ARS ribozyme to conjugate $^{Me}$Gly-DBE, $^{Me}$Ala-DBE and $^{Me}$Ser-DBE with tRNA. Enhanced flexizyme eFx was used with $^{Me}$Phe-CME.

tRNA$^{AsnE2}$ having GAU, GGC, GAG, GAA in the anticodon section were used in the process to assign the N-methyl amino acids $^{Me}$Gly, $^{Me}$Ala, $^{Me}$Ser, $^{Me}$Phe respectively to the codons AUU, GCU, CUU, UUU.

ARS ribozymes (25 mM), tRNA$^{AsnE2}$ (25 mM), 100 mM HEPES (pH 7.5), and 600 mM MgCl2 corresponding to the respective amino acid activation esters (5 mM) were added and aminoacylated at 0° C. for 2 hours ($^{Me}$Gly-DBE, $^{Me}$Ala-DBE) or 6 hours ($^{Me}$Ser-DBE, $^{Me}$Phe-CME), precipitated in ethanol, then used in translation.

An intramolecular S$_N$2 reaction between the chloroacetyl group and the sulfydryl group of cysteine situated in peptide is used to incorporate the cyclic structure into the peptide library. Accordingly, N-chloroacetyl-D-tryptophan (D-$^{ClAc}$Trp) was incorporated into the N terminal of peptide. Using the cyanomethyl ester of the present amino acid (D-$^{ClAc}$Trp-CME) and eFx, an aminoacyl tRNA formed by conjugating D-$^{ClAc}$Trp to an initiator tRNA$^{fMet-E}$ having an anticodon of CAU was prepared by the above reaction condition. The reaction of the amino acid lasted 2 hours.

Example 3

Construction of a Cyclic N-Methyl Peptide Library

To conjugate a puromycin linker Pu-CC-linker (5'-pCTC-CCGCCCCCCGTCC-(SPC18)$_5$CC-puromycin, bex Co. Ltd.) (SEQ ID NO: 22-(SPC18)$_5$CC-Pu) to the 3' terminal of the mRNA library, 10× Ligation buffer (TAKARA) 20 uL, H$_2$O 70 uL, DMSO 40 uL, 7.5 uM Pu-CC-linker 40 uL, 10 uM mRNA 20 uL, T4 RNA ligase (homemade) 10 uL were mixed and reacted at room temperature for 30 minutes. Then, 0.6 M NaCl and 10 mM EDTA 200 uL were added, and the reaction was terminated. The solution was processed with a phenol/chloroform solution, then precipitated with ethanol, dried, dissolved in H$_2$O 30 uL to form 6 uM mRNA-puromycin linker.

The translation of the peptide library was performed in an optimized in vitro translation system. The structure of the in vitro translation system is described below: 50 mM Hepes-KOH [pH 7.6], 100 mM KOAc, 20 mM Creatine phosphate, 12 mM Mg(OAc)$_2$, 2 mM GTP, 2 mM ATP, 1 mM CTP, 1 mM UTP, 2 mM Spermidine, 2 mM DTT, 100 uM 10-formyl-5,6,7,8-tetrahydroforlic acid (Baggott et al., 1995), 1.5 mg/mL E. coli total tRNA (Roche), 1.2 uM ribosome, 2.7 uM IF1, 0.4 uM IF2, 1.5 uM IF3, 30 uM EF-Tu, 30 uM EF-Ts, 0.26 uM EF-G, 0.25 uM RF2, 0.17 uM RF3, 0.5 uM RRF, 0.6 uM methionine transformylase, 4 ug/mL creatine kinase (Roche), 3 ug/mL myokinase (Sigma), 0.1 uM pyrophosphatase, 0.1 uM nucleotide-diphosphatase kinase, 0.1 uM T7 RNA polymerase.

The translation system further includes 12 types of aminoacyl tRNA synthetase (0.03 uM ArgRS, 0.38 uM AsnRS, 0.13 uM AspRS, 0.02 uM CysRS, 0.09 uM GlyRS, 0.02 uM HisRS, 0.11 uM LysRS (for Flag sequence), 0.16 uM ProRS, 0.04 uM SerRS, 0.09 uM ThrRS, 0.02 uM TyrRS, 0.02 uM ValRS) and 11 types of amino acids (arginine, asparagine, aspartic acid, cysteine, glycine, histidine, proline, serine, threonine, tyrosine, valine, at 0.2 mM each).

Further, the optimized in vitro translation above will be called Flexible In vitro Translation system (FIT system), since protein factors and amino acids can be removed freely (Unpublished Japanese patent application No. 2010-190315 by the same applicants). To 150 uL of FIT system were added 1.2 uM mRNA-puromycin linker and 5 aminoacyl tRNAs (D-$^{ClAc}$Trp-tRNA$^{fMet}{}_{UAC}$, $^{Me}$Gly-tRNA$^{AsnE2}{}_{GAU}$, $^{Me}$Ala-tRNA$^{AsnE2}{}_{GGC}$, $^{Me}$Ser-tRNA$^{AsnE2}{}_{GAG}$, $^{Me}$Phe-tRNA$^{AsnE2}{}_{GAA}$, 25 uM each), and translation was performed at 37° C. for 30 minutes to construct a cyclic N-methyl peptide library.

Figure 3:
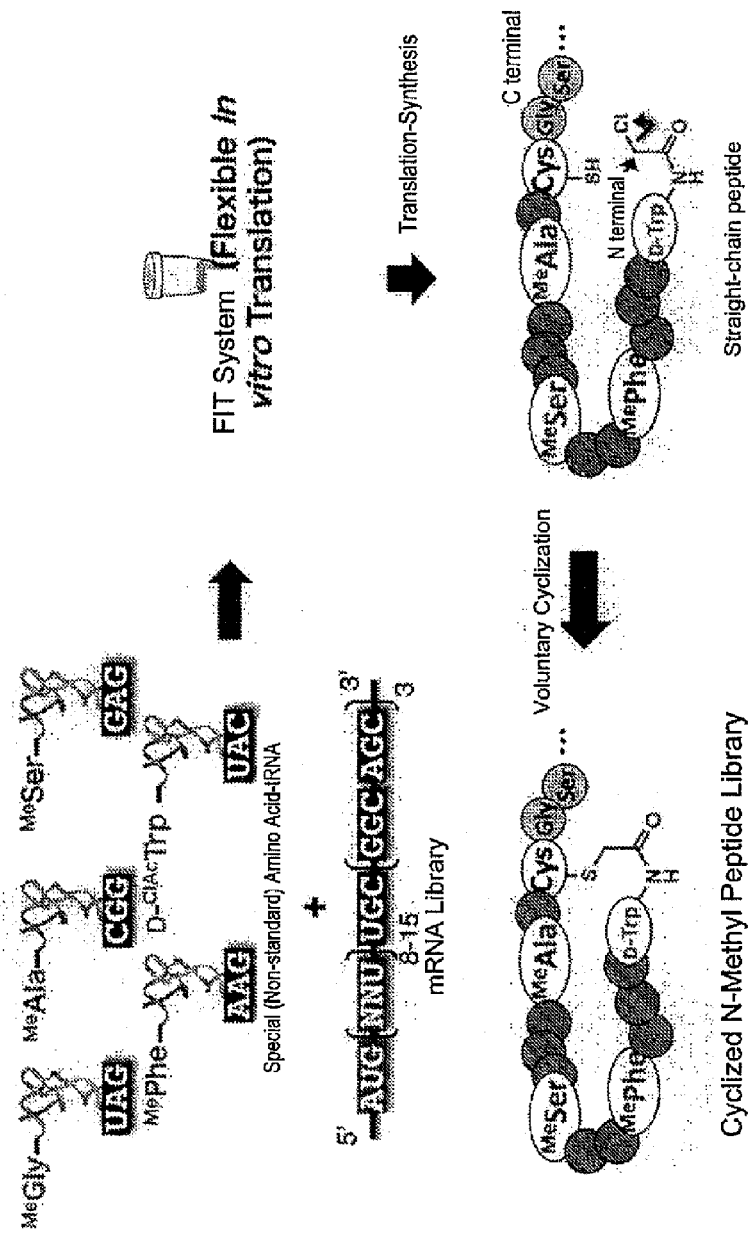
FIG. 3 shows the translation-synthesis of cyclic N-methyl peptide. (Example 3)

FIG. 3 shows the translation synthesis of the above cyclic N-methyl peptide.

The reaction product was left at room temperature for 12 minutes to conjugate mRNA-puromycin and peptide. Then, after 15 uL of 200 mM EDTA (pH 8.0) was added, it was left at 37° C. for 30 minutes to remove ribosome from mRNA. The solution was used as the mRNA-peptide complex solution for the first round of in vitro selection.

Meanwhile, the second round of library construction used 5 uL of translation solution. The rounds after the third used 2.5 uL of translation solution.

Example 4

In Vitro Selection

Figure 4:
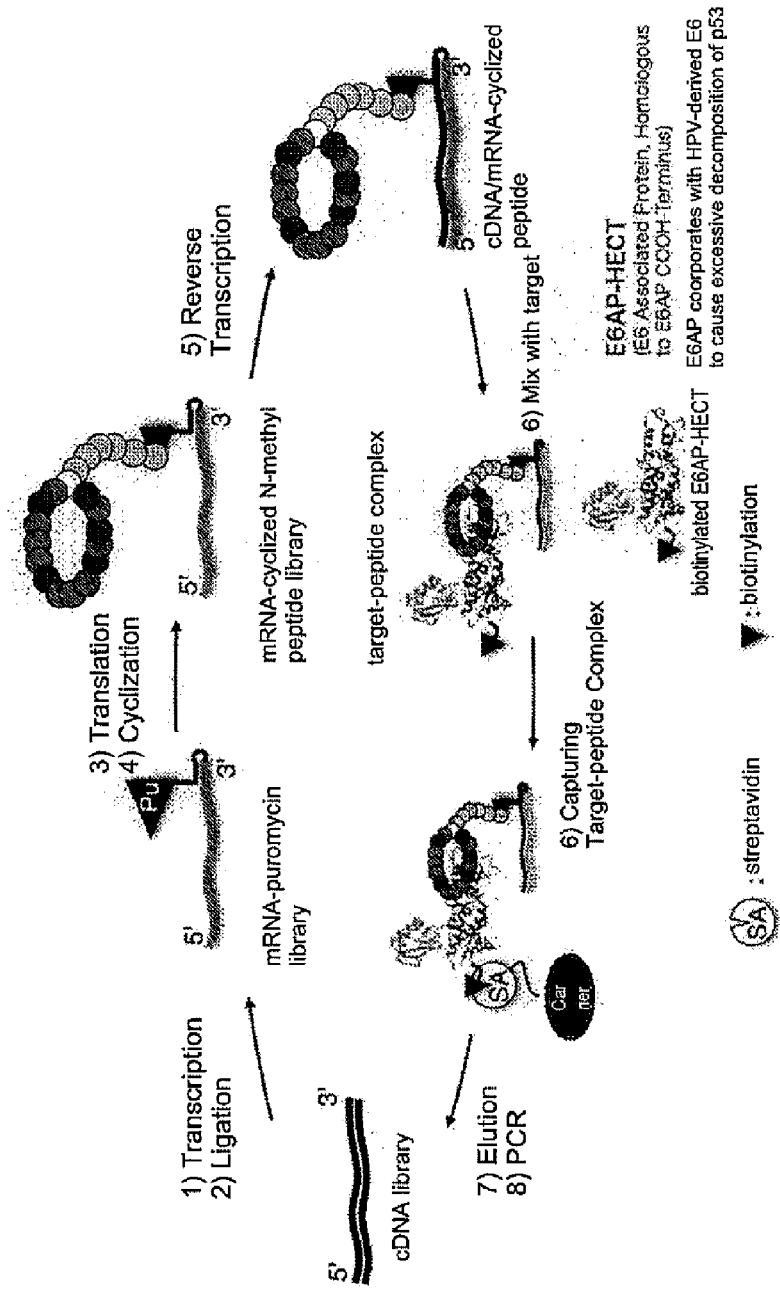
FIG. 4 explains a selection using a combination of the cyclic N-methyl peptide library and an mRNA display. (Example 4)

The biotinylated Avi-His-GB1-E6AP-HECT domain (Avi: biotinylated tag sequence, His: His$_6$ tag sequence, GB1: Protein GB1 domain, solubilizable tag sequence, Zhou et al. 2001) was fixed to the streptavidin-magnetic carrier (Invitrogen) to use for in vitro selection (FIG. 4).

The mRNA-peptide complex solution and E6AP-HECT fixing carrier (200 nM) of the first round were mixed and incubated at 4° C. for 30 minutes (positive selection). The supernatant was removed and 300 uL of iced TBST (100 mM Tris-HCl [pH 7.5], 300 mM NaCl, 0.05% (v/v) tween20) was washed. After the fixing carrier was recovered, 40 uL of the reverse transcription solution (5×RT buffer (Promega), 0.5 uM dNTPs, 2 uM CGS3an13R39, 5 U/uL MLV Reverse transcriptase (Promega), 0.2 U/uLRNase Inhibitor (Promega)) was added to perform reverse transcription by mixing at 42° C. for 1 hour. To the reverse transcription solution was added 360 uL of PCR solution (10 mM Tris-HCl [pH 7.5], 50 mM KCl, 0.1% (v/v) Triton X-100, 2.5 mM MgCl$_2$, 0.25 mM dNTPs, 0.25 uM T7g10M.F48, 0.25 uM CGS3an13R39), and the result was heated at 95° C. for 5 minutes, then the supernatant was recovered. Taq polymerase was added to the recovered solution, and the recovered cDNA was amplified by PCR. The amplified DNA was transcribed into mRNA for the next round. Further, the amount of recovered cDNA was obtained by real time PCR.

Meanwhile, after the second round, MLV reverse transcriptase (RNase H minus) was used for reverse transcription to form cDNA and mRNA-peptide complex to then perform in vitro selection. Then, in the second round, a carrier that is a mixture of a streptavidin magnetic carrier, a biotin fixing carrier, and an Avi-His-GB1 fixing carrier (200 nM) were mixed at a volume ratio of 1:1:1 and a mRNA-peptide complex solution were mixed at 4° C. for 30 minutes, and the above positive selection was performed using the supernatant. Then, the fixing carrier and PCR solution were mixed and heated, and the supernatant was recovered to amplify cDNA. Further in the third and fourth round, negative selection was performed 3 times before positive selection was performed at 37° C. Then, in the fifth and sixth round, the negative selection was performed 9 times before positive selection was performed at 37° C.

Rounds of selection were repeated until the cDNA recovery rate increased to 0.9% after the sixth round, then the sequence analysis of cDNA library was performed. The progress of selection is shown in FIG. 5-1.

Example 5

Confirmation of Translation Synthesis and Binding of MCP11

Figures 1, 5:
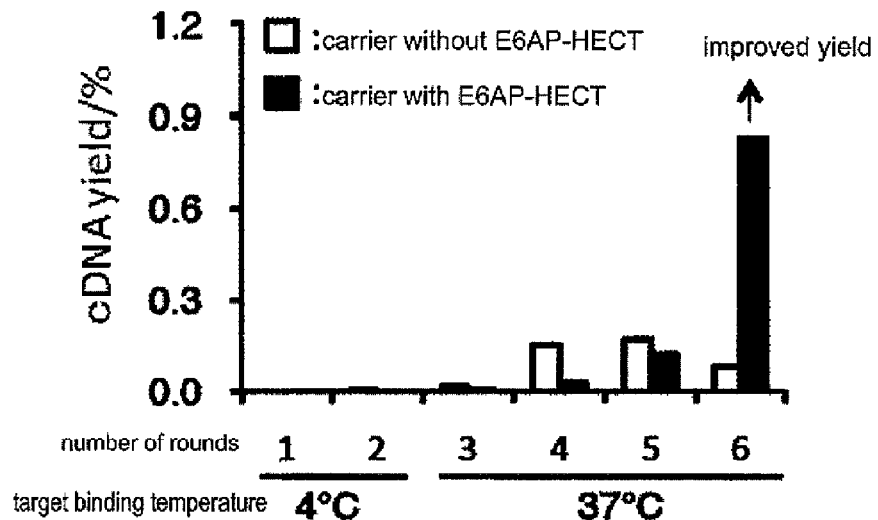
Figures 2, 5:
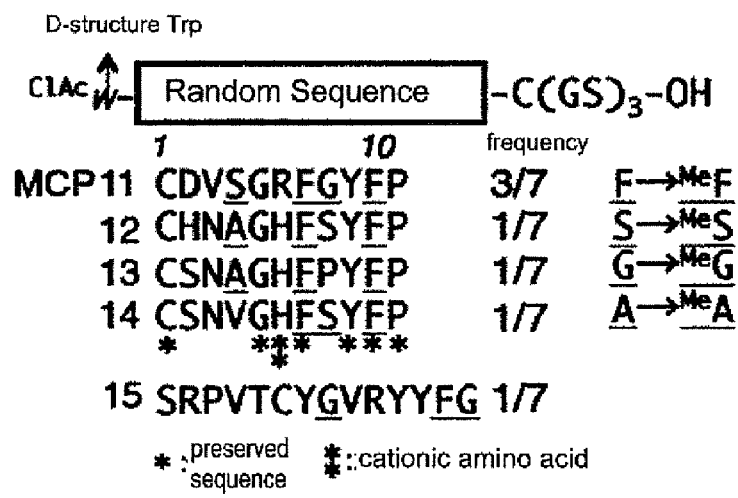
Figures 3, 4, 5:
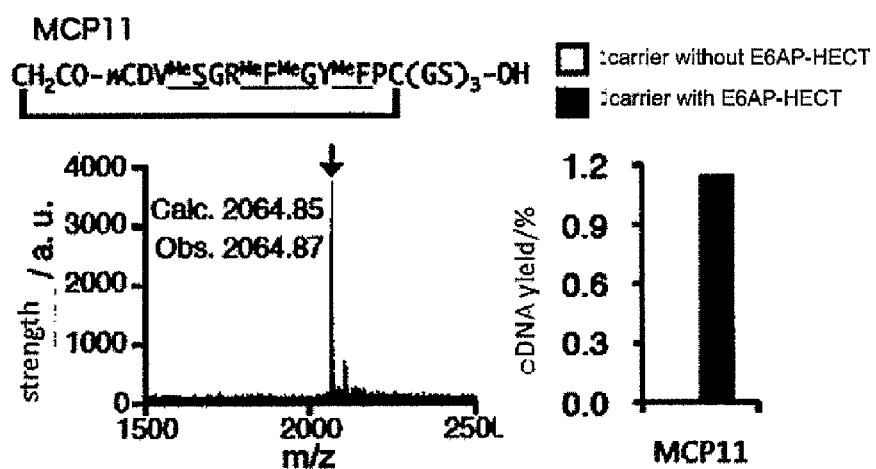

After sequence analysis, 5 peptide sequences were obtained; they were named MCP 11 to 15 (FIG. 5-2: analysis of peptide sequence from the DNA sequence).

Amino acid residues were preserved and 3 to 4 N-methyl amino acids were incorporated in MCP 11, 12, 13 and 14. MCP 15 includes 3 N-methyl amino acids; it has many hydrophobic residues and no preserved sequence with other clones. MCP 11, which was the largest in the number detected in the sequence analysis, was further experimented.

The random sequence of MCP11 included a sequence consisting of an amino acid sequence CDVSGRFGYFP (the underlined S, F, and G are N-methyls). The structure cyclized by the binding of $^{ClAc}$W and C of the D-system is shown below.

[Formula 14]

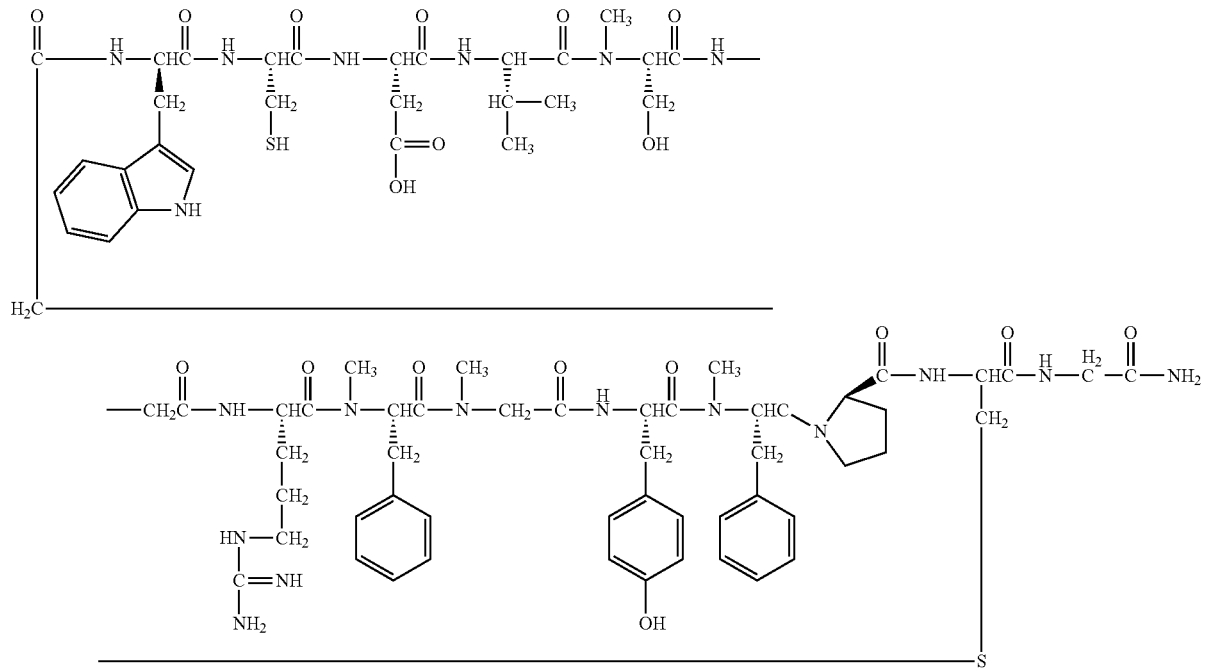

To confirm whether MCP11 was accurately translation-synthesized by the FIT system, a mass analysis was performed by MALDI-TOF analysis. A straight chain DNA was amplified from a plasmid of MCP11 containing cDNA by a PCR that uses T7g10M.F48 (5'-TAATACGACTCACTAT-AGGGTTAACTTTAAGAAGGAGATATACATATG-3') SEQ ID NO: 7 as the forward primer and CGS3an13TAA.R39 (5'-TTTCCGCCCCCCGTCTTAGCT-GCCGCTGCCGCTGCCGCA-3') SEQ ID NO: 25 as the reverse primer.

The peptide translation terminates by RF2 (release factor 2, translation release factor 2) in the FIT system when the terminator codon is changed from UAG to UAA, and an increase in the peptide yield can be expected.

The straight chain cDNA and 5 aminoacyl tRNAs (D-$^{ClAc}$Trp-tRNA$^{fMet}_{UAC}$, $^{Me}$Gly-tRNA$^{AsnE2}_{GAU}$, $^{Me}$Ala-tRNA$^{AsnE2}_{GGC}$, $^{Me}$Ser-tRNA$^{AsnE2}_{GAG}$, $^{Me}$Phe-tRNA$^{AsnE2}_{GAA}$, each at 25 uM) were added to the FIT system and translation was performed at 37° C. for 30 minutes. The translation solution was desalted with a C18 chip column, and analyzed with MALDI-TOF. The obtained extract mass is 2064.87, and the translation-synthesis of the desired peptide (calculated exact mass=2064.85) was confirmed. The left panel of FIG. 5-3 should be referred to.

Then, using a single cDNA (comprising UAG) of MCP11, an evaluation of binding to E6AP-HECT through the mRNA display method (transcription, conjugation of a puromycin linker, a reverse transcription, a binding to the target, a recovery of cDNA, evaluation by real-time PCR) was performed. Translation was performed at a scale of 2.5 uL, and the negative selection (for a carrier with no E6AP-HECT) was performed at 4° C. for 3 times and a positive selection (for a carrier with E6AP-HECT) was performed at 37° C. As a result, it was confirmed that cDNA was recovered and MCP11 specifically bound to E6AP-HECT in positive selection. Refer to the right panel in FIG. 5-3.

Example 6

Peptide Synthesis and Refinement

Based on the sequence information obtained by selection, a corresponding MCP11 was synthesized by the Fmoc peptide solid phase synthesis method. Peptide on the resin was precipitated by ether after being cleaved by a solution of trifluoroacetic acid: triisopropylsilane: H$_2$O (87.5:10:2.5). The precipitate was dissolved in a 50% acetonitrile (1% trifluoroacetic acid) solution, to which triethylamine was added, and a cyclic reaction was performed under a basic condition. Then, the product was refined by HPLC using a C18 reversed column. The refined peptide was dissolved in DMSO after being frozen and dried. The molecular weight of obtained peptide was measured by MALDI-TOF MS.

Example 7

Determination of Binding Constant Using SPR

The binding constant of MCP11 to E6AP-HECT was analyzed by a surface plasmon resonance using BIACORE T100. A streptavidin sensor chip (SA chip certified) was used as a sensor chip, an Avi-His-GB1-E6AP-HECT was used as a ligand, and MCP11 was used as an analyte. After E6AP-HECT was fixed to a sensor chip, the KD of MCP11 was 0.5 nM. Further, the KD of a straight chain N-methyl peptide MLP11 was 100 to 1000 nM, exhibiting a difference in the binding ability of 200 times or more. Further, the cyclic peptide CP11 and the straight chain peptide LP11, which include no N-methyl amino acids, did not bind at 1000 nM.

The result showed that the N-methyl skeleton and the macrocyclic skeleton of MCP11 are mandatory for a strong binding to E6AP-HECT (FIG. 5-4: Affinity analysis of MCP11 and a derivative by the surface plasmon resonance).

SEQUENCE LISTING FREE TEXT

SEQ ID NO: 1 Fx
SEQ ID NO: 2 dFx
SEQ ID NO: 3 eFx
SEQ ID NO: 4 aFx
SEQ ID NO: 5 tRNA$^{Asn-E2}$
SEQ ID NO: 6 tRNA$^{fMet-E}$
SEQ ID NO: 7 T7g10M.F48
SEQ ID NO: 8 CGS3an13.R39
SEQ ID NO: 9 tRNA$^{Asn}$
SEQ ID NO: 10 tRNA$^{fMet}$
SEQ ID NO: 11 NNUpool 8. R69
SEQ ID NO: 12 NNUpool 9. R72
SEQ ID NO: 13 NNUpool 10. R75
SEQ ID NO: 14 NNUpool 11. R78
SEQ ID NO: 15 NNUpool 12. R81
SEQ ID NO: 16 NNUpool 13. R84
SEQ ID NO: 17 NNUpool 14. R87
SEQ ID NO: 18 NNUpool 15. R90
SEQ ID NO: 19 Epsilon Sequence
SEQ ID NO: 20 peptide linker
SEQ ID NO: 21 Pu linker CS
SEQ ID NO: 22 Pu linker oligonucleotide
SEQ ID NO: 23 random DNA generic sequence
SEQ ID NO: 24 random RNA generic sequence
SEQ ID NO: 25 CGS3an13TAA.R39

---

The invention claimed is:

1. A method for selecting a non-standard peptide comprising multiple N-methyl amino acids that specifically binds to a target substance from a peptide library, comprising the steps of:
   (i) generating a peptide library by:
      a) preparing a nucleic acid library comprising coding nucleic acids with each coding nucleic acid including a random sequence consisting of multiple different triplets, wherein at least one of the triplets in each of the random sequences correspond to artificial codons that specify N-methyl amino acids;
      b) translating the nucleic acid library by an in vitro translation system wherein pairing of an anticodon of elongator tRNA acylated by a N-methyl amino acid and an artificial codon specifying the N-methyl amino acid occurs, and
      c) thereby obtaining a peptide library of at least $10^{13}$ types of peptides including non-standard peptides with randomly incorporated N-methyl amino acids, wherein each peptide in the peptide library and the coding nucleic acid are linked to form an in vitro display peptide library,
   (ii) bringing the peptide library in contact with a target substance; and
   (iii) selecting a non-standard peptide comprising multiple N-methyl amino acids that specifically binds to the target substance.

2. The method according to claim 1, wherein step (iii) comprises recovering coding nucleic acids that display the selected peptides bound to the target substance, determining a nucleotide sequence of the coding nucleic acids, determining the peptide sequence from the nucleotide sequence, and selecting a non-standard peptide that specifically binds to the target substance comprising multiple N-methyl amino acids.

3. The method according to claim 1, wherein the step (i) comprises acylating an elongator tRNA with a N-methyl amino acid using an RNA catalyst having an acyl-tRNA synthetase-like activity, to obtain an elongator tRNA acylated by the N-methyl amino acid.

4. The method according to claim 1, wherein the elongator tRNA acylated by a N-methyl amino acid is an artificial tRNA prepared by an in vitro transcription.

5. The method according to claim 1, wherein the nucleic acid library is a library of mRNAs.

6. The method according to claim 1, wherein
each coding nucleic acid further includes sequences corresponding to
a codon specifying an amino acid having Functional Group 1, and
a codon specifying an amino acid having Functional Group 2, and
Functional Group 1 and Functional Group 2 are a pair of functional groups that are capable of bond forming reaction, and in the step (i), cyclic special peptides are included in the peptide library by a bond forming reaction between Functional Group 1 and Functional Group 2.

7. The method according to claim 1, wherein each triplet constituting the random sequence is selected from codons having the following sequences:
an $N^1N^2U$ codon {wherein $N^1$ and $N^2$ are independently one of A, U, C or G};
an $N^1N^2K$ codon {wherein $N^1$ and $N^2$ are independently one of A, U, C or G, and K is either C or G};
an $N^1N^2N^3$ codon {wherein $N^1$, $N^2$ and $N^3$ are independently one of A, U, C or G}.

8. The method according to claim 7, wherein the random sequence consists of 2 or more repetitions of one of the $N^1N^2U$ codon, the $N^1N^2K$ codon and the $N^1N^2N^3$ codon.

9. The method according to claim 6, wherein Functional Group 1 and Functional Group 2 are one of (A) to (C) below, which are pairs of functional groups:

[Formula 1]

(A)

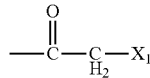
(A-1)

HS— (A-2)

(B)
(B-1)

(B-2)

(C)
(C-1)

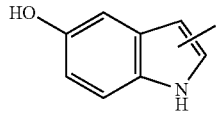
(C-2)

(wherein, $X_1$ is either Cl or Br, and Ar is an aromatic ring that can comprise a substituent).

10. The method according to claim 6, wherein the amino acid having Functional Group 1 is an amino acid having a chloroacetyl group and the amino acid having Functional Group 2 is cysteine.

11. The method according to claim 10, wherein the each coding nucleic acid comprises (a) to (c) below:
(a) an initiator codon specifying an amino acid having a chloroacetyl group,
(b) a random sequence consisting of repetitions of an NNU {wherein, N is one ribonucleotide of A, U, C or G} codon, which comprises one or more artificial codons specifying N-methyl amino acids, and
(c) a codon specifying cysteine,
wherein the amino acid having a chloroacetyl group is incorporated in the N terminal of the peptide by pairing of the initiator codon and an anticodon of an initiator tRNA acylated by the amino acid having a chloroacetyl group,
and one or more N-methyl amino acids are incorporated in the peptide by pairing of each artificial codon specifying a N-methyl amino acid in the random sequence and an anticodon of an elongator tRNA acylated by a special the N-methyl amino acid, and the translation products, which are the peptides, are cyclized by a bond forming reaction between the chloroacetyl group and a sulfhydryl group of cysteine.

12. The method according to claim 1, wherein the in vitro display peptide library is selected from a group consisting of ribosome display library, an mRNA display library, a RAPID display library, or a PD display library.

* * * * *

SEQUENCE LISTING

```
<160> NUMBER OF SEQ ID NOS: 25

<210> SEQ ID NO 1
<211> LENGTH: 45
<212> TYPE: RNA
<213> ORGANISM: Artificial
<220> FEATURE:
<223> OTHER INFORMATION: Fx

<400> SEQUENCE: 1
ggaucgaaag auuuccgcag gcccgaaagg guauuggcgu uaggu            45

<210> SEQ ID NO 2
<211> LENGTH: 46
<212> TYPE: RNA
<213> ORGANISM: Artificial
<220> FEATURE:
<223> OTHER INFORMATION: dFx

<400> SEQUENCE: 2
ggaucgaaag auuuccgcau ccccgaaagg guacauggcg uuaggu           46

<210> SEQ ID NO 3
<211> LENGTH: 45
<212> TYPE: RNA
<213> ORGANISM: Artificial
<220> FEATURE:
<223> OTHER INFORMATION: eFx

<400> SEQUENCE: 3
ggaucgaaag auuuccgcgg ccccgaaagg ggauuagcgu uaggu            45

<210> SEQ ID NO 4
<211> LENGTH: 47
<212> TYPE: RNA
<213> ORGANISM: Artificial
<220> FEATURE:
<223> OTHER INFORMATION: aFx

<400> SEQUENCE: 4
ggaucgaaag auuuccgcac ccccgaaagg gguaaguggc guuaggu          47

<210> SEQ ID NO 5
<211> LENGTH: 76
<212> TYPE: RNA
<213> ORGANISM: Artificial
<220> FEATURE:
<223> OTHER INFORMATION: tRNAAsn-E2
<220> FEATURE:
```

```
<221> NAME/KEY: misc_feature
<222> LOCATION: (34)..(36)
<223> OTHER INFORMATION: n stands for any base

<400> SEQUENCE: 5
ggcucuguag uucagucggu agaacggcgg acunnnaauc cguaugucac ugguucgagu    60
ccagucagag ccgcca                                                    76

<210> SEQ ID NO 6
<211> LENGTH: 77
<212> TYPE: RNA
<213> ORGANISM: Artificial
<220> FEATURE:
<223> OTHER INFORMATION: tRNA fMet-E

<400> SEQUENCE: 6
ggcggggugg agcagccugg uagcucgucg ggcucauaac ccgaagaucg ucgguucaaa    60
uccggccccc gcaacca                                                   77

<210> SEQ ID NO 7
<211> LENGTH: 48
<212> TYPE: DNA
<213> ORGANISM: Artificial
<220> FEATURE:
<223> OTHER INFORMATION: T7g10M.F48

<400> SEQUENCE: 7
taatacgact cactataggg ttaactttaa gaaggagata tacatatg                 48

<210> SEQ ID NO 8
<211> LENGTH: 39
<212> TYPE: DNA
<213> ORGANISM: Artificial
<220> FEATURE:
<223> OTHER INFORMATION: CGS3an13.R39

<400> SEQUENCE: 8
tttccgcccc ccgtcctagc tgccgctgcc gctgccgca                           39

<210> SEQ ID NO 9
<211> LENGTH: 76
<212> TYPE: RNA
<213> ORGANISM: Escherichia coli
<220> FEATURE:
<223> OTHER INFORMATION: tRNAAsn
<220> FEATURE:
<221> NAME/KEY: misc_feature
<222> LOCATION: (8)..(8)
<223> OTHER INFORMATION: n stands for a modified base
<220> FEATURE:
<221> NAME/KEY: modified_base
<222> LOCATION: (8)..(8)
<223> OTHER INFORMATION: s4u
<220> FEATURE:
<221> NAME/KEY: misc_feature
<222> LOCATION: (16)..(16)
<223> OTHER INFORMATION: n stands for a modified base
<220> FEATURE:
<221> NAME/KEY: modified_base
<222> LOCATION: (16)..(16)
<223> OTHER INFORMATION: d
<220> FEATURE:
<221> NAME/KEY: misc_feature
<222> LOCATION: (20)..(20)
<223> OTHER INFORMATION: n stands for a modified base
<220> FEATURE:
<221> NAME/KEY: modified_base
<222> LOCATION: (20)..(20)
<223> OTHER INFORMATION: d
```

```
<220> FEATURE:
<221> NAME/KEY: misc_feature
<222> LOCATION: (34)..(34)
<223> OTHER INFORMATION: n stands for a modified base
<220> FEATURE:
<221> NAME/KEY: modified_base
<222> LOCATION: (34)..(34)
<223> OTHER INFORMATION: q
<220> FEATURE:
<221> NAME/KEY: misc_feature
<222> LOCATION: (37)..(37)
<223> OTHER INFORMATION: n stands for a modified base
<220> FEATURE:
<221> NAME/KEY: modified_base
<222> LOCATION: (37)..(37)
<223> OTHER INFORMATION: t6a
<220> FEATURE:
<221> NAME/KEY: misc_feature
<222> LOCATION: (39)..(39)
<223> OTHER INFORMATION: n stands for a modified base
<220> FEATURE:
<221> NAME/KEY: modified_base
<222> LOCATION: (39)..(39)
<223> OTHER INFORMATION: p
<220> FEATURE:
<221> NAME/KEY: misc_feature
<222> LOCATION: (46)..(46)
<223> OTHER INFORMATION: n stands for a modified base
<220> FEATURE:
<221> NAME/KEY: modified_base
<222> LOCATION: (46)..(46)
<223> OTHER INFORMATION: m7g
<220> FEATURE:
<221> NAME/KEY: misc_feature
<222> LOCATION: (54)..(54)
<223> OTHER INFORMATION: n stands for a modified base
<220> FEATURE:
<221> NAME/KEY: modified_base
<222> LOCATION: (54)..(54)
<223> OTHER INFORMATION: t
<220> FEATURE:
<221> NAME/KEY: misc_feature
<222> LOCATION: (55)..(55)
<223> OTHER INFORMATION: n stands for a modified base
<220> FEATURE:
<221> NAME/KEY: modified_base
<222> LOCATION: (55)..(55)
<223> OTHER INFORMATION: p

<400> SEQUENCE: 9
uccucugnag uucagncggn agaacggcgg acunuunanc cguaunucac uggnncgagu    60
ccagucagag gagcca                                                   76

<210> SEQ ID NO 10
<211> LENGTH: 77
<212> TYPE: RNA
<213> ORGANISM: Escherichia coli
<220> FEATURE:
<223> OTHER INFORMATION: tRNAfMet
<220> FEATURE:
<221> NAME/KEY: misc_feature
<222> LOCATION: (8)..(8)
<223> OTHER INFORMATION: n stands for a modified base
<220> FEATURE:
<221> NAME/KEY: modified_base
<222> LOCATION: (8)..(8)
<223> OTHER INFORMATION: s4u
<220> FEATURE:
<221> NAME/KEY: misc_feature
<222> LOCATION: (21)..(21)
<223> OTHER INFORMATION: n stands for a modified base
<220> FEATURE:
<221> NAME/KEY: modified_base
<222> LOCATION: (21)..(21)
<223> OTHER INFORMATION: d
<220> FEATURE:
```

```
<221> NAME/KEY: misc_feature
<222> LOCATION: (33)..(33)
<223> OTHER INFORMATION: n stands for a modified base
<220> FEATURE:
<221> NAME/KEY: modified_base
<222> LOCATION: (33)..(33)
<223> OTHER INFORMATION: cm
<220> FEATURE:
<221> NAME/KEY: misc_feature
<222> LOCATION: (55)..(55)
<223> OTHER INFORMATION: n stands for a modified base
<220> FEATURE:
<221> NAME/KEY: modified_base
<222> LOCATION: (55)..(55)
<223> OTHER INFORMATION: t
<220> FEATURE:
<221> NAME/KEY: misc_feature
<222> LOCATION: (56)..(56)
<223> OTHER INFORMATION: n stands for a modified base
<220> FEATURE:
<221> NAME/KEY: modified_base
<222> LOCATION: (56)..(56)
<223> OTHER INFORMATION: p

<400> SEQUENCE: 10
cgcggggngg agcagccugg nagcucgucg ggnucauaac ccgaagaucg ucggnncaaa    60
uccggccccc gcaacca                                                  77

<210> SEQ ID NO 11
<211> LENGTH: 69
<212> TYPE: DNA
<213> ORGANISM: Artificial
<220> FEATURE:
<223> OTHER INFORMATION: NNUpool 8. R69
<220> FEATURE:
<221> NAME/KEY: misc_feature
<222> LOCATION: (23)..(45)
<223> OTHER INFORMATION: n stands for any base

<400> SEQUENCE: 11
gctgccgctg ccgctgccgc aannannann annannanna nnanncatat gtatatctcc    60
ttcttaaag                                                           69

<210> SEQ ID NO 12
<211> LENGTH: 72
<212> TYPE: DNA
<213> ORGANISM: Artificial
<220> FEATURE:
<223> OTHER INFORMATION: NNUpool 9. R72
<220> FEATURE:
<221> NAME/KEY: misc_feature
<222> LOCATION: (23)..(48)
<223> OTHER INFORMATION: n stands for any base

<400> SEQUENCE: 12
gctgccgctg ccgctgccgc aannannann annannanna nnannannca tatgtatatc    60
tccttcttaa ag                                                       72

<210> SEQ ID NO 13
<211> LENGTH: 75
<212> TYPE: DNA
<213> ORGANISM: Artificial
<220> FEATURE:
<223> OTHER INFORMATION: NNUpool 10. R75
<220> FEATURE:
<221> NAME/KEY: misc_feature
<222> LOCATION: (23)..(51)
<223> OTHER INFORMATION: n stands for any base

<400> SEQUENCE: 13
```

```
gctgccgctg ccgctgccgc aannannann annannanna nnannannan ncatatgtat    60
atctccttct taaag                                                     75

<210> SEQ ID NO 14
<211> LENGTH: 78
<212> TYPE: DNA
<213> ORGANISM: Artificial
<220> FEATURE:
<223> OTHER INFORMATION: NNUpool 11. R78
<220> FEATURE:
<221> NAME/KEY: misc_feature
<222> LOCATION: (23)..(54)
<223> OTHER INFORMATION: n stands for any base

<400> SEQUENCE: 14
gctgccgctg ccgctgccgc aannannann annannanna nnannannan nanncatatg    60
tatatctcct tcttaaag                                                  78

<210> SEQ ID NO 15
<211> LENGTH: 81
<212> TYPE: DNA
<213> ORGANISM: Artificial
<220> FEATURE:
<223> OTHER INFORMATION: NNUpool 12. R81
<220> FEATURE:
<221> NAME/KEY: misc_feature
<222> LOCATION: (23)..(57)
<223> OTHER INFORMATION: n stands for any base

<400> SEQUENCE: 15
gctgccgctg ccgctgccgc aannannann annannanna nnannannan nannanncat    60
atgtatatct ccttcttaaa g                                              81

<210> SEQ ID NO 16
<211> LENGTH: 84
<212> TYPE: DNA
<213> ORGANISM: Artificial
<220> FEATURE:
<223> OTHER INFORMATION: NNUpool 13. R84
<220> FEATURE:
<221> NAME/KEY: misc_feature
<222> LOCATION: (23)..(60)
<223> OTHER INFORMATION: n stands for any base

<400> SEQUENCE: 16
gctgccgctg ccgctgccgc aannannann annannanna nnannannan nannannann    60
catatgtata tctccttctt aaag                                           84

<210> SEQ ID NO 17
<211> LENGTH: 87
<212> TYPE: DNA
<213> ORGANISM: Artificial
<220> FEATURE:
<223> OTHER INFORMATION: NNUpool 14. R87
<220> FEATURE:
<221> NAME/KEY: misc_feature
<222> LOCATION: (23)..(63)
<223> OTHER INFORMATION: n stands for any base

<400> SEQUENCE: 17
gctgccgctg ccgctgccgc aannannann annannanna nnannannan nannannann    60
anncatatgt atatctcctt cttaaag                                        87

<210> SEQ ID NO 18
```

```
<211> LENGTH: 90
<212> TYPE: DNA
<213> ORGANISM: Artificial
<220> FEATURE:
<223> OTHER INFORMATION: NNUpool 15. R90
<220> FEATURE:
<221> NAME/KEY: misc_feature
<222> LOCATION: (23)..(66)
<223> OTHER INFORMATION: n stands for any base

<400> SEQUENCE: 18
gctgccgctg ccgctgccgc aannannann annannanna nnannannan nannannann        60
annanncata tgtatatctc cttcttaaag                                         90

<210> SEQ ID NO 19
<211> LENGTH: 10
<212> TYPE: RNA
<213> ORGANISM: Artificial
<220> FEATURE:
<223> OTHER INFORMATION: Epsilon Sequence

<400> SEQUENCE: 19
uuaacuuuaa                                                               10

<210> SEQ ID NO 20
<211> LENGTH: 18
<212> TYPE: RNA
<213> ORGANISM: Artificial
<220> FEATURE:
<223> OTHER INFORMATION: peptide linker

<400> SEQUENCE: 20
ggcagcggca gcggcagc                                                      18

<210> SEQ ID NO 21
<211> LENGTH: 18
<212> TYPE: RNA
<213> ORGANISM: Artificial
<220> FEATURE:
<223> OTHER INFORMATION: Pu linker CS

<400> SEQUENCE: 21
uaggacgggg ggcggaaa                                                      18

<210> SEQ ID NO 22
<211> LENGTH: 16
<212> TYPE: DNA
<213> ORGANISM: Artificial
<220> FEATURE:
<223> OTHER INFORMATION: Pu linker oligonucleotide

<400> SEQUENCE: 22
ctcccgcccc ccgtcc                                                        16

<210> SEQ ID NO 23
<211> LENGTH: 90
<212> TYPE: DNA
<213> ORGANISM: Artificial
<220> FEATURE:
<223> OTHER INFORMATION: random DNA generic sequence
<220> FEATURE:
<221> NAME/KEY: promoter
<222> LOCATION: (1)..(18)
<223> OTHER INFORMATION:
<220> FEATURE:
<221> NAME/KEY: misc_signal
<222> LOCATION: (21)..(30)
<223> OTHER INFORMATION:
```

```
<220> FEATURE:
<221> NAME/KEY: misc_signal
<222> LOCATION: (32)..(38)
<223> OTHER INFORMATION:
<220> FEATURE:
<221> NAME/KEY: misc_feature
<222> LOCATION: (49)..(51)
<223> OTHER INFORMATION: n stands for any base, and the triplet nnt
      represents a repeat codon

<400> SEQUENCE: 23
taatacgact cactataggg ttaactttaa gaaggagata tacatatgnn ttgcggcagc     60
ggcagcggca gctaggacgg ggggcggaaa                                     90

<210> SEQ ID NO 24
<211> LENGTH: 73
<212> TYPE: RNA
<213> ORGANISM: Artificial
<220> FEATURE:
<223> OTHER INFORMATION: random RNA generic sequence
<220> FEATURE:
<221> NAME/KEY: misc_signal
<222> LOCATION: (4)..(13)
<223> OTHER INFORMATION:
<220> FEATURE:
<221> NAME/KEY: misc_signal
<222> LOCATION: (15)..(21)
<223> OTHER INFORMATION:
<220> FEATURE:
<221> NAME/KEY: misc_feature
<222> LOCATION: (32)..(34)
<223> OTHER INFORMATION: n stands for any base, and the nnu triplet
      represents a repeat codon

<400> SEQUENCE: 24
ggguuaacuu uaagaaggag auauacauau gnnuugcggc agcggcagcg gcagcuagga    60 cgggggggcgg aaa                                                      73

<210> SEQ ID NO 25
<211> LENGTH: 39
<212> TYPE: DNA
<213> ORGANISM: Artificial
<220> FEATURE:
<223> OTHER INFORMATION: CGS3an13TAA.R39

<400> SEQUENCE: 25
tttccgcccc ccgtcttagc tgccgctgcc gctgccgca                           39
```